United States Patent
Bandman et al.

(10) Patent No.: US 6,632,617 B1
(45) Date of Patent: Oct. 14, 2003

(54) TUMOR-ASSOCIATED ANTIGEN

(75) Inventors: Olga Bandman, Mountain View, CA (US); Surya K. Goli, San Jose, CA (US); Purvi Shah, San Jose, CA (US); Neil C. Corley, Castro Valley, CA (US); David G. Streeter, Boulder Creek, CA (US)

(73) Assignee: Incyte Corporation, Palo Alto, CA (US)

( * ) Notice: Subject to any disclaimer, the term of this patent is extended or adjusted under 35 U.S.C. 154(b) by 38 days.

(21) Appl. No.: 09/855,288

(22) Filed: May 14, 2001

Related U.S. Application Data

(60) Continuation-in-part of application No. 09/439,563, filed on Nov. 12, 1999, now abandoned, which is a division of application No. 09/227,224, filed on Jan. 8, 1999, now Pat. No. 6,350,581, which is a division of application No. 08/855,261, filed on May 13, 1997, now Pat. No. 5,922,566.

(51) Int. Cl.$^7$ .......................... C07K 16/00; G01N 33/53
(52) U.S. Cl. .......................... 435/7.1; 435/4; 530/387.1; 530/388.1
(58) Field of Search .................... 435/7.1, 4; 530/387.1, 530/388.1

(56) References Cited

PUBLICATIONS

Helzlsouer, K.J., "Epidemiology, prevention, and early detection of breast cancer", *Curr. Opin. Oncol.*, 6: 541–548 (1994).

Harris, J.R. et al., "Breast Cancer", *N. Engl. J. Med.*, 327: 319–328 (1992).

Minegishi, M. et al., "Monoclonal Antibody Directed To Human T–Cell Malignancy Antigen", *Leukemia Res.*, 13: 43–51 (1989).

Takagi, S. et al., "Identification Of A Highly Specific Surface Marker Of T–Cell Acute Lymphoblastic Leukemia And Neuroblastoma As A New Member Of The Transmembrane 4 Superfamily", *Int. J. Cancer*, 61: 706–715 (1995).

Liu, E. et al., "The HER2 (c–erbB–2) oncogene is frequently amplified in in situ carcinomas of the breast", *Oncogene*, 7: 1027–1032 (1992).

Kern, J.A. et al., "Inhibition of Human Lung Cancer Cell Line Growth by an Anti–p185$^{HER2}$ Antibody", *Am. J. Respir. Cell Mol. Biol.*, 9: 448–454 (1993).

Wright, M.D. et al., "The ins and outs of the transmembrane 4 superfamily", *Immunol. Today*, 15: 588–594 (1994).

Jankowski, S.A. et al., "SAS, a gene amplified in human sarcomas, encodes a new member of the transmembrane 4 superfamily of proteins", *Oncogene*, 9: 1205–1211 (1994).

Miyake, M. et al., "A Specific Cell Surface Glycoconjugate Controlling Cell Motility: Evidence by Functional Monoclonal Antibodies That Inhibit Cell Motility and Tumor Cell Metastasis", *Biochem.*, 30: 3328–3334 (1991).

Marken, J.S. et al., "Cloning and expression of the tumor–associated antigen L6", *Proc. Natl. Acad. Sci. USA*, 89: 3503–3507 (1992).

Marken, J.S. et al., "Membrane Topology of the L6 Antigen and Identification of the Protein Epitope Recognized by the L6 Monoclonal Antibody", *J. Biol. Chem.*, 269: 7397–7401 (1994).

Marken, J.S. et al., (Direct Submission), GenBank Sequence Database (Accession 186804), National Center for Biotechnology Information, (GI 186804) (Apr. 24, 1993).

Marken, J.S. et al., (Direct Submission), GenBank Sequence Database (Accession 476343), National Center for Biotechnology Information, (GI 476343) (May 2, 1994).

Mueller–Pillasch et al., (Direct Submission) GenBank Sequence Database (Accession AAB82947), National Center for Biotechnology Information (GI 2587054) (Nov. 6, 1997).

*Primary Examiner*—Sean McGarry
(74) *Attorney, Agent, or Firm*—Incyte Corporation

(57) ABSTRACT

The invention provides a cDNA which encodes a TUAN. It also provides for the use of the cDNA, fragments, complements, and variants thereof and of the encoded protein, portions thereof and antibodies thereto for diagnosis and treatment of inflammatory and cell proliferative disorders, in particular, Crohn's disease and colon cancer. The invention additionally provides expression vectors and host cells for the production of the protein and a transgenic model system.

11 Claims, 4 Drawing Sheets

Figure 3A:
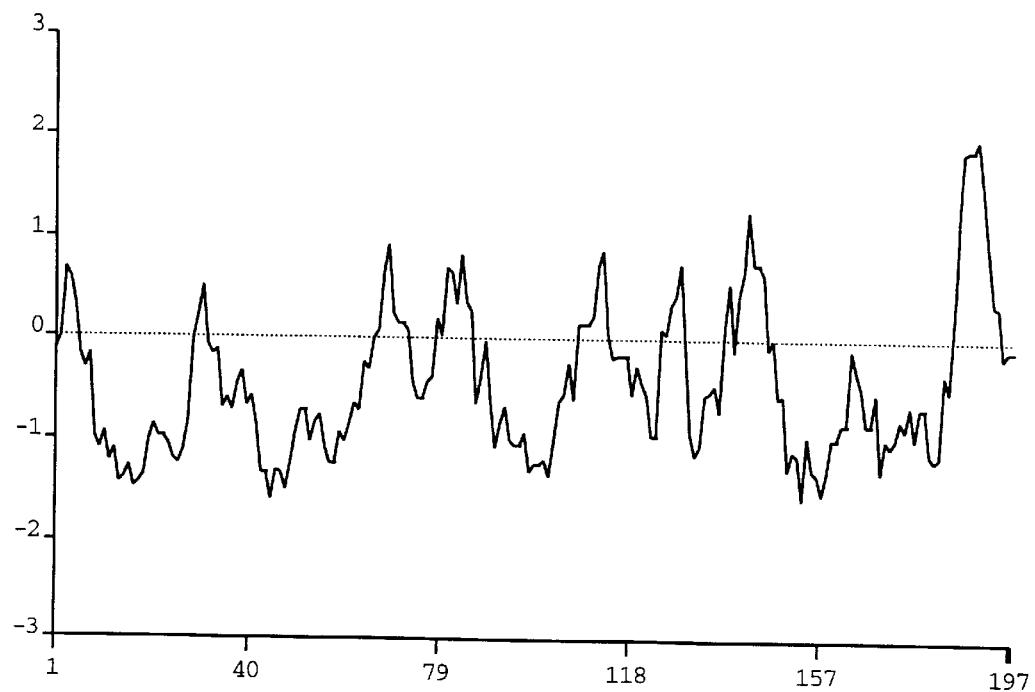

```
                                                                                54
                                                  36           45    
                           27                     ATG  ACG  GGA  AAA  TGT  GCC
       9         18        CAC  CTC  ACC          M    T    G    K    C    A
5' NCG GCT CGA GCG GCT CGA GCC TGA
                                                                                108
                                                  90           99
                                                  CTC  TGC  ATT  GTG  GCC  AAC
           63        72        81                 L    C    I    V    A    N
CGC TGT GTG GGG CTC TCC CTC ATT ACC CTC
R   C   V   G   L   S   L   I   T   L
                                                                                162
                                                  144          153
                                                  GAG  ACC  TCC  ACC  AAC  CAT  CTC
       117       126       135                    E    T    S    T    N    H    L
GCC CTC CTG CTG GTA CCT AAT GGG
A   L   L   L   V   P   N   G
                                                                                216
                                                  198          207
                                                  GGC  GGG  TTC  ATT  GGC  CTA  ATG  GTA  CTG
       171       180       189                    G    G    F    I    G    L    M    V    L
AGC TTG CAA GTC CTC TGG ATG
S   L   Q   V   L   W   M
                                                                                270
                                                  252          261
                                                  GCA  GGG  GGC  AAG  GGC  TGT  GGT  GCT  GGG
       225       234       243                    A    G    G    K    G    C    G    A    G
TGT CCA GGG ATT GCA GCC GTT CGG
C   P   G   I   A   A   V   R
                                                                                324
                                                  306          315
                                                  CGC  TCG  GTC  TTC  TCC  TCG  GCG  TTC  GGG
       279       288       297                    R    S    V    F    S    S    A    F    G
TGC TGT GGA AAC CGC TGC AGG ATG CTG
C   C   G   N   R   C   R   M   L
                                                                                378
                                                  360          369
                                                  GGA  GCT  GGG  CTC  CGA  AAT  GGA
       333       342       351                    G    A    G    L    R    N    G
GTG CTT GGT GCC ATC TAC TGC CTG TCG GTG TCT                                     432
V   L   G   A   I   Y   C   L   S   V   S
                387       396       405       414                     423

FIGURE 1A
```

```
CCC AGA TGC TTA ATG AAC GGC GAG TGG GGC TAC CAC TTC GAA GAC ACC GCG GGA
P   R   C   L   M   N   G   E   W   G   Y   H   F   E   D   T   A   G
                                        441                             486
GCT TAC TTG CTC AAC CGC ACT CTA TGG GAT CGG TGC GAG GCG CCC CCT CGC GTG
A   Y   L   L   N   R   T   L   W   D   R   C   E   A   P   P   R   V
                                        495                             540
GTC CCC TGG AAT GTG ACG CTC TTC TCG CTG CTG CTG GCC GCC TCC TGC CTG GAG
V   P   W   N   V   T   L   F   S   L   L   L   A   A   S   C   L   E
                                        549                             594
ATA GTA CTG TGT GGG ATC CAG CTG GTG AAC GCG ACC ATT GGT GTC TTC TGC GGC
I   V   L   C   G   I   Q   L   V   N   A   T   I   G   V   F   C   G
                                        603                             648
GAT TGC AGG AAA AAA CAG GAC ACA CCT CAC TGA GGC TCC ACT GAC CGC CGG GTT
D   C   R   K   K   Q   D   T   P   H   *
                                        657                             702
ACA CCT GCT CCT TCC TGG ACG CTC CTC GCT AGA ATA AAC TGC TTT
                                        711
GCG CTC TCT T 3'
```

FIGURE 1B

| | | |
|---|---|---|
| 1   MCTGKCARCVGLSLITLCLVCIVANALLLVPNGETSWTNT | 1634851 |
| 1   MCYGKCARCIGHSLVGLALLCIAANILLYFPNGETKYASE | GI 186804 |
| 1   MCYVKCARYIGYSLVWAAVFCIVANALLYFPNGETKYATE | GI 476343 |
| | |
| 41  NHLSLQVWLMGGFIGGGLMVLCPGIAAVRAGGKGCCGAGC | 1634851 |
| 41  NHLSRFVWFFSGIVGGGLMLLPAFVFIGLEQDDCCG---C | GI 186804 |
| 41  DHLSRFVWYFAGIVGGGLMLLPAFVFIGMDEEDCCG---C | GI 476343 |
| | |
| 81  CG----NRCRMLRSVFSSAFGVLGAIYCLSVSGAGLRNG | 1634851 |
| 79  CGHENCGKRCAMLSSVLAALIGIAGSGYCVIVAALGLAEG | GI 186804 |
| 79  CGYENYGKRCSMLSSVLAALIGIVGSAYCVIVASLGLAEG | GI 476343 |
| | |
| 116 PRCL-MNGEWGYHFEDTAGAYLLNRTLWDRCEAPPRVVPW | 1634851 |
| 119 PLCLDSLGQWNYTFASTEGQYLLDTSTWSECTEPKHIVEW | GI 186804 |
| 119 PKCSDAHGVWNYTFASTEGQYLLNSSMWSKCYEPKHIVEW | GI 476343 |
| | |
| 155 NVTLFSLLVAASCLEIVLCGIQLVNATIGVFCGDC-RKKQ | 1634851 |
| 159 NVSLFSILLALGGIEFILCLIQVINGVLGGICGGFCCSHQQ | GI 186804 |
| 159 HVTLFSILLAFAAVEFILCLIQVINGMLGGLCGYCCSRQQ | GI 476343 |
| | |
| 194 DTPH | 1634851 |
| 199 QYDC | GI 186804 |
| 199 QYNC | GI 476343 |

FIGURE 2

SEQUENCE LISTING

<160> NUMBER OF SEQ ID NOS: 10

<210> SEQ ID NO 1
<211> LENGTH: 197

```
<212> TYPE: PRT
<213> ORGANISM: Homo sapiens
<220> FEATURE:
<221> NAME/KEY: misc_feature
<223> OTHER INFORMATION: Incyte ID No: 1634851CD1

<400> SEQUENCE: 1

Met Cys Thr Gly Lys Cys Ala Arg Cys Val Gly Leu Ser Leu Ile
 1               5                  10                  15

Thr Leu Cys Leu Val Cys Ile Val Ala Asn Ala Leu Leu Leu Val
                20                  25                  30

Pro Asn Gly Glu Thr Ser Trp Thr Asn Thr Asn His Leu Ser Leu
                35                  40                  45

Gln Val Trp Leu Met Gly Gly Phe Ile Gly Gly Gly Leu Met Val
                50                  55                  60

Leu Cys Pro Gly Ile Ala Ala Val Arg Ala Gly Gly Lys Gly Cys
                65                  70                  75

Cys Gly Ala Gly Cys Cys Gly Asn Arg Cys Arg Met Leu Arg Ser
                80                  85                  90

Val Phe Ser Ser Ala Phe Gly Val Leu Gly Ala Ile Tyr Cys Leu
                95                 100                 105

Ser Val Ser Gly Ala Gly Leu Arg Asn Gly Pro Arg Cys Leu Met
               110                 115                 120

Asn Gly Glu Trp Gly Tyr His Phe Glu Asp Thr Ala Gly Ala Tyr
               125                 130                 135

Leu Leu Asn Arg Thr Leu Trp Asp Arg Cys Glu Ala Pro Pro Arg
               140                 145                 150

Val Val Pro Trp Asn Val Thr Leu Phe Ser Leu Leu Val Ala Ala
               155                 160                 165

Ser Cys Leu Glu Ile Val Leu Cys Gly Ile Gln Leu Val Asn Ala
               170                 175                 180

Thr Ile Gly Val Phe Cys Gly Asp Cys Arg Lys Lys Gln Asp Thr
               185                 190                 195

Pro His

<210> SEQ ID NO 2
<211> LENGTH: 711
<212> TYPE: DNA
<213> ORGANISM: Homo sapiens
<220> FEATURE:
<221> NAME/KEY: misc_feature
<223> OTHER INFORMATION: Incyte ID No: 1634851CB1

<400> SEQUENCE: 2
cggctcgagc ggctcgagcc tgacacctca ccatgtgtac gggaaaatgt gcccgctgtg      60
tggggctctc cctcattacc ctctgcctcg tctgcattgt ggccaacgcc ctcctgctgg     120
tacctaatgg ggagacctcc tggaccaaca ccaaccatct cagcttgcaa gtctggctca     180
tgggcggctt cattggcggg ggcctaatgg tactgtgtcc aggattgca gccgttcggg      240 caggggcaa gggctgctgt ggtgctgggt gctgtggaaa ccgctgcagg atgctgcgct     300
cggtcttctc ctcggcgttc ggggtgcttg gtgccatcta ctgcctctcg gtgtctggag     360
ctgggctccg aaatggaccc agatgcttaa tgaacggcga gtggggctac cacttcgaag     420
acaccgcggg agcttacttg ctcaaccgca ctctatggga tcggtgcgag gcgccccctc     480
gcgtggtccc ctggaatgtg acgctcttct cgctgctggt ggccgcctcc tgcctggaga     540
tagtactgtg tgggatccag ctggtgaacg cgaccattgg tgtcttctgc ggcgattgca     600
```

```
ggaaaaaaca ggacacacct cactgaggct ccactgaccg ccgggttaca cctgctcctt    660
cctggacgct cactcccttg ctcgctagaa taaactgctt tgcgctctct t             711
```

<210> SEQ ID NO 3
<211> LENGTH: 543
<212> TYPE: DNA
<213> ORGANISM: Homo sapiens
<220> FEATURE:
<221> NAME/KEY: misc_feature
<223> OTHER INFORMATION: Incyte ID No: 1634851F6

<400> SEQUENCE: 3

```
ccgcctgtcc ttcctgacac ctcaccatgt gtacgggaaa atgtgcccgc tgtgtggggc    60
tctccctcat taccctctgc ctcgtctgca ttgtggccaa cgccctcctg ctggtaccta    120
atggggagac ctcctggacc aacaccaacc atctcagctt gcaagtctgg ctcatgggcg    180
gcttcattgg cggggcccta atggtactgt gtccggggat tgcagccgtt cgggcagggg    240
gcaagggctg ctgtggtgct gggtgctgtg gaaaccgctg caggatgctg cgctcggtct    300
tctcctcggc gttcggggtg cttggtgcca tctactgcct ctcggtgtct ggagctgggc    360
tccgaaatgg acccagatgc ttaatgaacg gcgagtgggg ctaccattcg aagacaccgc    420
gggagcttac ttgctcaacc gcactctatg ggatcggtgc gaggcgcccc tcgcgtggtc    480
ccctggaaat gtgaacgtct ctcgctgctg gtggccgct  tctgctggag atataatgtg    540
tgg                                                                  543
```

<210> SEQ ID NO 4
<211> LENGTH: 422
<212> TYPE: DNA
<213> ORGANISM: Homo sapiens
<220> FEATURE:
<221> NAME/KEY: misc_feature
<223> OTHER INFORMATION: Incyte ID No: 1634851T6
<221> NAME/KEY: unsure
<222> LOCATION: 5, 12-13, 190, 337, 339, 379
<223> OTHER INFORMATION: a, t, c, g, or other

<400> SEQUENCE: 4

```
gagcntccag gnnggagcag gtgtaacccg gcggtcagtg gagcctcagt gaggtgtgtc    60
ctgttttttc ctgcaatcgc cgcagaagac accaatggtc gcgttcacca gctggatccc    120
acacagtact atctccaggc aggaggcggc caccagcagc gagaagagcg tcacattcca    180
ggggaccacn cgagggggcg cctcgcaccg atcccataga gtgcggttga gcaagtaagc    240
tcccgcggtg tcttcgaagt ggtagcccca ctcgccgttc attaagcatc tgggtccatt    300
tcggagccca gctccagaca ccgagaggca gtagatngna ccaagcaccc cgaacgcccg    360
cagagaagac cgagcgcana tcctgcaagc ggtttccaca gcaccccagc acccacagca    420
gc                                                                   422
```

<210> SEQ ID NO 5
<211> LENGTH: 292
<212> TYPE: DNA
<213> ORGANISM: Rattus norvegicus
<220> FEATURE:
<221> NAME/KEY: misc_feature
<223> OTHER INFORMATION: Incyte ID No: 700275672H1

<400> SEQUENCE: 5

```
gcctttccgg acgcctcagg catgtgtact ggaaagtgtg ctcgatgcct ggggctctcc    60
```

-continued

```
ctcatccctc tctccctgat ctgcatcgtg gccaatgccc tcctgctggt acctgatggg      120
aagaccacat tgacggatgg caacctcagc ttgcaagttt ggctcatggg cggcttcatt      180
ggagggggct tgatggtgct gtgccctgga attgctgcag tccgggccgg gggaaagggc      240
tgctgcggtg caggctgctg tgggaaccgc tgcaggatgc tgcgctctgt ct             292
```

<210> SEQ ID NO 6
<211> LENGTH: 150
<212> TYPE: DNA
<213> ORGANISM: Rattus norvegicus
<220> FEATURE:
<221> NAME/KEY: misc_feature
<223> OTHER INFORMATION: Incyte ID No: 700308846H1

<400> SEQUENCE: 6

```
acggcttcat tggagggggc ttgatggtgc tgtgccctgg aattgctgca gtccgggccg       60
ggggaaaggg ctgctgcggt gcaggctgct gtgggaaccg ctgcaggatg ctgcgctctg      120
tcttctcctc cgcctttggg atacttggtg                                      150
```

<210> SEQ ID NO 7
<211> LENGTH: 372
<212> TYPE: DNA
<213> ORGANISM: Rattus norvegicus
<220> FEATURE:
<221> NAME/KEY: misc_feature
<223> OTHER INFORMATION: Incyte ID No: 700308171F6

<400> SEQUENCE: 7

```
gcaggagctg ggctcgaagt gggacccaaa tgcttaataa ataacaaatg ggactaccac       60
ttccaagaaa cccaaggcgg ttacttgcac aatgacactc tttggaattt atgtgaggcg      120
ccacctcacg tggtaccctg aatgtgacg ctcttctcaa ttctggtggt cgcctcaagt      180
ctggaaacag tgttgtgcgg aatacagctg gtgaatgcga cctttggcgt gttgtgtggc      240
gattgccggt aaaaggagg gctcagctca ctgagttcca tgggcctacc cttaatacct      300
catttctgga agtcggagcg gtcacccact cccctgggtg gctagaaaaa aaaccttagt      360
ggaataaaca gc                                                          372
```

<210> SEQ ID NO 8
<211> LENGTH: 405
<212> TYPE: DNA
<213> ORGANISM: Homo sapiens
<220> FEATURE:
<221> NAME/KEY: misc_feature
<223> OTHER INFORMATION: GenBank ID No: g989099
<221> NAME/KEY: unsure
<222> LOCATION: 2, 8-10, 68, 293, 314, 357, 372
<223> OTHER INFORMATION: a, t, c, g, or other

<400> SEQUENCE: 8

```
tnatatannn gcgcaaagca gttttattct agcgagcaag ggagtgagcg tccaggaagg       60
agcaggtnta acccggcggt cagtggagcc tcagtgaggt gtgtcctgtt ttttcctgca      120
atcgccgcag aagacaccaa tggtcgcgtt caccagctgg atcccacaca gtactatctc      180
caggcaggag gcggccacca gcagcgagaa gagcgtcaca ttccagggga ccacgcgagg      240 ggcgcctcg accgatccca tagagtgcgg ttgagcaagt aagctcccgc gtntcttcga      300
agtggtagcc ccantcgccg ttcattaagc atctgggtcc atttcggagc ccagttncag      360
gacaccgaga gncagtagat ggcaccaagc accccgaacg ccgag                     405
```

-continued

```
<210> SEQ ID NO 9
<211> LENGTH: 202
<212> TYPE: PRT
<213> ORGANISM: Homo sapiens
<220> FEATURE:
<221> NAME/KEY: misc_feature
<223> OTHER INFORMATION: GenBank ID No: g186804

<400> SEQUENCE: 9

Met Cys Tyr Gly Lys Cys Ala Arg Cys Ile Gly His Ser Leu Val
 1               5                  10                  15

Gly Leu Ala Leu Leu Cys Ile Ala Ala Asn Ile Leu Leu Tyr Phe
                20                  25                  30

Pro Asn Gly Glu Thr Lys Tyr Ala Ser Glu Asn His Leu Ser Arg
                35                  40                  45

Phe Val Trp Phe Phe Ser Gly Ile Val Gly Gly Leu Leu Met
                50                  55                  60

Leu Leu Pro Ala Phe Val Phe Ile Gly Leu Glu Gln Asp Asp Cys
                65                  70                  75

Cys Gly Cys Cys Gly His Glu Asn Cys Gly Lys Arg Cys Ala Met
                80                  85                  90

Leu Ser Ser Val Leu Ala Ala Leu Ile Gly Ile Ala Gly Ser Gly
                95                 100                 105

Tyr Cys Val Ile Val Ala Ala Leu Gly Leu Ala Glu Gly Pro Leu
               110                 115                 120

Cys Leu Asp Ser Leu Gly Gln Trp Asn Tyr Thr Phe Ala Ser Thr
               125                 130                 135

Glu Gly Gln Tyr Leu Leu Asp Thr Ser Thr Trp Ser Glu Cys Thr
               140                 145                 150

Glu Pro Lys His Ile Val Glu Trp Asn Val Ser Leu Phe Ser Ile
               155                 160                 165

Leu Leu Ala Leu Gly Gly Ile Glu Phe Ile Leu Cys Leu Ile Gln
               170                 175                 180

Val Ile Asn Gly Val Leu Gly Gly Ile Cys Gly Phe Cys Cys Ser
               185                 190                 195

His Gln Gln Gln Tyr Asp Cys
               200

<210> SEQ ID NO 10
<211> LENGTH: 202
<212> TYPE: PRT
<213> ORGANISM: Mus musculus
<220> FEATURE:
<221> NAME/KEY: misc_feature
<223> OTHER INFORMATION: GenBank ID No: g476343

<400> SEQUENCE: 10

Met Cys Tyr Val Lys Cys Ala Arg Tyr Ile Gly Tyr Ser Leu Val
 1               5                  10                  15

Trp Ala Ala Val Phe Cys Ile Val Ala Asn Ala Leu Leu Tyr Phe
                20                  25                  30

Pro Asn Gly Glu Thr Lys Tyr Ala Thr Glu Asp His Leu Ser Arg
                35                  40                  45

Phe Val Trp Tyr Phe Ala Gly Ile Val Gly Gly Leu Leu Met
                50                  55                  60

Leu Leu Pro Ala Phe Val Phe Ile Gly Met Asp Glu Glu Asp Cys
                65                  70                  75

Cys Gly Cys Cys Gly Tyr Glu Asn Tyr Gly Lys Arg Cys Ser Met
```

```
                         80                   85                   90
Leu Ser Ser Val Leu Ala Ala Leu Ile Gly Ile Val Gly Ser Ala
                     95                  100                  105
Tyr Cys Val Ile Val Ala Ser Leu Gly Leu Ala Glu Gly Pro Lys
                    110                  115                  120
Cys Ser Asp Ala His Gly Val Trp Asn Tyr Thr Phe Ala Ser Thr
                    125                  130                  135
Glu Gly Gln Tyr Leu Leu Asn Ser Ser Met Trp Ser Lys Cys Tyr
                    140                  145                  150
Glu Pro Lys His Ile Val Glu Trp His Val Thr Leu Phe Ser Ile
                    155                  160                  165
Leu Leu Ala Phe Ala Ala Val Glu Phe Ile Leu Cys Leu Ile Gln
                    170                  175                  180
Val Ile Asn Gly Met Leu Gly Gly Leu Cys Gly Tyr Cys Cys Ser
                    185                  190                  195
Arg Gln Gln Gln Tyr Asn Cys
                    200
```

US 6,632,617 B1

TUMOR-ASSOCIATED ANTIGEN

This application is a continuation-in-part of application U.S. Ser. No. 09/439,563, filed Nov. 12, 1999 and now abandoned, which is a divisional application of U.S. Ser. No. 09/227,224, filed Jan. 8, 1999 and now U.S. Pat. No. 6,350,581, which is a divisional application U.S. Ser. No. 08/855,261 and now filed May 13, 1997 U.S. Pat. No. 5,922,566, issued Jul. 13, 1999, all of which applications and patents are hereby incorporated by reference.

FIELD OF THE INVENTION

This invention relates to a cDNA which encodes tumor-associated antigen and to the use of the cDNA and the encoded protein in the diagnosis and treatment of inflammatory and cell proliferative disorders, in particular, Crohn's disease and colon cancer.

BACKGROUND OF THE INVENTION

Phylogenetic relationships among organisms have been demonstrated many times, and studies from a diversity of prokaryotic and eukaryotic organisms suggest a more or less gradual evolution of molecules, biochemical and physiological mechanisms, and metabolic pathways. Despite different evolutionary pressures, the proteins of nematode, fly, rat, and man have common chemical and structural features and generally perform the same cellular function. Comparisons of the nucleic acid and protein sequences from organisms where structure and/or function are known accelerate the investigation of human sequences and allow the development of model systems for testing diagnostic and therapeutic agents for human conditions, diseases, and disorders.

Cancers, or malignant tumors, which are characterized by continuous cell proliferation and cell death, can be classified into three categories: carcinomas, sarcomas, and leukemia. Recent reports show that approximately one in eight women contracts breast cancer and that the risk of prostate cancer is about 9.5% among men over 50 years of age (Helzlsouer (1994) Curr Opin Oncol 6: 541–548; Harris et al. (1992) N Engl J Med 327:319–328). Cancer cells have been shown to exhibit unique gene expression, and many cancer-specific genetic markers, tumor antigens, have been identified.

Tumor antigens are surface molecules that are differentially expressed in tumor cells relative to non-tumor tissues. Tumor antigens make tumor cells immunologically distinct from normal cells and provide diagnostic and therapeutic targets for human cancers. Several monoclonal antibodies have been identified which react specifically with cancerous cells such as T-cell acute lymphoblastic leukemia and neuroblastoma (Minegishi et al. (1989) Leukemia Res 13:43–51; Takagi et al. (1995) Int J Cancer 61: 706–715). In addition, the discovery of high level expression of the HER2 gene in breast tumors has led to the development of therapeutic treatments (Liu et al. (1992) Oncogene 7: 1027–1032; Kern (1993) Am J Respir Cell Mol Biol 9:448–454).

Tumor antigens have been characterized either as membrane proteins or as altered carbohydrate molecules of glycoproteins or glycolipids on the cell surface. A multigene family encoding type III integral membrane proteins which traverse the cell membrane four times has been identified (Wright and Tomlinson (1994) Immunol Today 15:588–94). The transmembrane 4 superfamily (TM4SF) proteins are found predominantly in cells of hematopoietic origin and in tumors and include a number of platelet and endothelial cell membrane proteins; CD9 (lung adenocarcinoma antigen MRP-1), the platelet and melanoma-associated antigen CD63, leukocyte surface glycoproteins, CD53, CD37, CD63, and R2, the tumor associated antigen TAPA-1 (CD81), the colonal carcinoma antigen CO-029, mink lung epithelial protein TI-1, and the tumor-associated antigens L6 and SAS, a gene amplified in human sarcomas (Wright and Tomlinson, supra; Jankowski et al. (1994) Oncogene 9:1205–1211). These proteins all share 25–30% amino acid sequence identity.

In the TM4SF proteins, the N- and C-termini are intracellular and the major hydrophilic domain, located between transmembrane domains 3 and 4, is extracellular. TM4SF proteins are most conserved in their transmembrane and cytoplasmic domains and most divergent in their hydrophilic extracellular domains which contain N-linked glycosylation sites. The high level of conservation in the transmembrane and cytoplasmic domains suggests an effector/signaling function. The divergence of the extracellular domains suggests that these hydrophilic domains provide functions specific to each protein such as ligand binding or protein-protein interaction (Wright and Tomlinson, supra).

A number of TM4SF proteins have been implicated in signal transduction, control of cell adhesion, and regulation of cell growth and proliferation (Wright and Tomlinson, supra; Jankowski, supra). Expression of some TM4SF proteins is associated with a variety of tumors and is altered when cells are activated or dividing. Other TM4SF proteins are implicated in cell growth due to their association with tumor cells. For example, CD9, CD53, and CD82 are upregulated when lymphocytes are activated while the expression of CD37 is abolished when B cells are activated. Although CD9 is not expressed on resting B and T lymphocytes, it is a marker for 90% of non-T acute lymphoblastic leukemia cells and for 50% of acute myeloid and chronic lymphoid leukemias. Anti-CD9 antibodies inhibit the motility of a variety of cancer cell lines and inhibit the metastatic potential of the mouse BL6 cell line (Miyake and Hakomori (1991) Biochem 30:3328–3334). Similarly, CD63 is not expressed on normal tissue melanocytes, but it is expressed in early stage melanoma. Another member of the TM4SF superfamily, the L6 surface antigen, is differentially expressed on lung, breast, colon, and ovarian carcinomas. This antigen is an attractive target for therapeutic intervention due to its high level of expression on malignant cells (Marken et al. (1992) Proc Natl Acad Sci USA 89: 3503–3507; Marken et al. (1994) J Biol Chem 269: 7397–7401).

The discovery of a cDNA encoding tumor-associated antigen similar to the tumor-associated L6 antigen satisfies a need in the art by providing compositions which are useful in the diagnosis and treatment of inflammatory and cell proliferative disorders, in particular, Crohn's disease and colon cancer.

SUMMARY OF THE INVENTION

The invention is based on the discovery of a cDNA encoding tumor-associated antigen (TUAN) which is useful in the diagnosis and treatment of inflammatory and cell proliferative disorders, in particular, Crohn's disease and colon cancer.

The invention provides an isolated cDNA comprising a nucleic acid sequence encoding a protein having the amino acid sequence of SEQ ID NO:1. The invention also provides an isolated cDNA or the complement thereof selected from the group consisting of a nucleic acid sequence of SEQ ID NO:2, a fragment of SEQ ID NO:2 selected from SEQ ID NOs:34, and a variant of SEQ ID NO:2 selected from SEQ ID NOs:5–7. The invention additionally provides a composition, a substrate, and a probe comprising the cDNA, or the complement of the cDNA, encoding TUAN. The invention further provides a vector containing the cDNA, a host cell containing the vector and a method for using the cDNA to make TUAN. The invention still further provides a transgenic cell line or organism comprising the vector containing the cDNA encoding TUAN. The invention additionally provides a fragment, a variant, or the complement of the cDNA selected from the group consisting of SEQ ID Nos:2–7. In one aspect, the invention provides a substrate containing at least one of these fragments or variants or the complements thereof. In a second aspect, the invention provides a probe comprising a cDNA or the complement thereof which can be used in methods of detection, screening, and purification. In a further aspect, the probe is a single-stranded complementary RNA or DNA molecule.

The invention provides a method for using a cDNA to detect the differential expression of a nucleic acid in a sample comprising hybridizing a probe to the nucleic acids, thereby forming hybridization complexes and comparing hybridization complex formation with a standard, wherein the comparison indicates the differential expression of the cDNA in the sample. In one aspect, the method of detection further comprises amplifying the nucleic acids of the sample prior to hybridization. In another aspect, the method showing differential expression of the cDNA is used to diagnose inflammatory and cell proliferative disorders, in particular, Crohn's disease and colon cancer. In another aspect, the cDNA or a fragment or a variant or the complements thereof may comprise an element on an array.

The invention additionally provides a method for using a cDNA or a fragment or a variant or the complements thereof to screen a library or plurality of molecules or compounds to identify at least one ligand which specifically binds the cDNA, the method comprising combining the cDNA with the molecules or compounds under conditions allowing specific binding, and detecting specific binding to the cDNA, thereby identifying a ligand which specifically binds the cDNA. In one aspect, the molecules or compounds are selected from aptamers, DNA molecules, RNA molecules, peptide nucleic acids, artificial chromosome constructions, peptides, transcription factors, repressors, and regulatory molecules.

The invention provides a purified protein or a portion thereof selected from the group consisting of an amino acid sequence of SEQ ID NO:1, a variant having at least 85% identity to the amino acid sequence of SEQ ID NO:1, an antigenic epitope of SEQ ID NO:1, and a biologically active portion of SEQ ID NO:1. The invention also provides a composition comprising the purified protein and a pharmaceutical carrier. The invention further provides a method of using the TUAN to treat a subject with inflammatory and cell proliferative disorders, in particular, Crohn's disease and colon cancer comprising administering to a patient in need of such treatment the composition containing the purified protein. The invention still further provides a method for using a protein to screen a library or a plurality of molecules or compounds to identify at least one ligand, the method comprising combining the protein with the molecules or compounds under conditions to allow specific binding and detecting specific binding, thereby identifying a ligand which specifically binds the protein. In one aspect, the molecules or compounds are selected from DNA molecules, RNA molecules, peptide nucleic acids, peptides, proteins, mimetics, agonists, antagonists, antibodies, immunoglobulins, inhibitors, and drugs. In another aspect, the ligand is used to treat a subject with inflammatory and cell proliferative disorders, in particular, Crohn's disease and colon cancer.

The invention provides a method of using a protein to screen a subject sample for antibodies which specifically bind the protein comprising isolating antibodies from the subject sample, contacting the isolated antibodies with the protein under conditions that allow specific binding, dissociating the antibody from the bound-protein, and comparing the quantity of antibody with known standards, wherein the presence or quantity of antibody is diagnostic of inflammatory and cell proliferative disorders, in particular, Crohn's disease and colon cancer.

The invention also provides a method of using a protein to prepare and purify antibodies comprising immunizing a animal with the protein under conditions to elicit an antibody response, isolating animal antibodies, attaching the protein to a substrate, contacting the substrate with isolated antibodies under conditions to allow specific binding to the protein, dissociating the antibodies from the protein, thereby obtaining purified antibodies.

The invention provides a purified antibody which binds specifically to a protein which is expressed in inflammatory and cell proliferative disorders, in particular, Crohn's disease and colon cancer. The invention also provides a method of using an antibody to diagnose inflammatory and cell proliferative disorders, in particular, Crohn's disease and colon cancer comprising combining the antibody comparing the quantity of bound antibody to known standards, thereby establishing the presence of inflammatory and cell proliferative disorders, in particular, Crohn's disease and colon cancer. The invention further provides a method of using an antibody to treat inflammatory and cell proliferative disorders, in particular, Crohn's disease and colon cancer comprising administering to a patient in need of such treatment a composition comprising the purified antibody and a pharmaceutical carrier.

The invention provides a method for inserting a heterologous marker gene into the genomic DNA of a mammal to disrupt the expression of the endogenous polynucleotide. The invention also provides a method for using a cDNA to produce a mammalian model system, the method comprising constructing a vector containing the cDNA selected from SEQ ID NOs:2–7, transforming the vector into an embryonic stem cell, selecting a transformed embryonic stem cell, microinjecting the transformed embryonic stem cell into a mammalian blastocyst, thereby forming a chimeric blastocyst, transferring the chimeric blastocyst into a pseudopregnant dam, wherein the dam gives birth to a chimeric offspring containing the cDNA in its germ line, and breeding the chimeric mammal to produce a homozygous, mammalian model system.

BRIEF DESCRIPTION OF THE FIGURES AND TABLE

FIGS. 1A and 1B show the TUAN (SEQ ID NO:1) encoded by the cDNA (SEQ ID NO:2). The alignment was produced using MACDNASIS PRO software (Hitachi Software Engineering, South San Francisco Calif.).

FIG. 2 demonstrates the conserved chemical and structural similarities among the sequences and domains of TUAN (1634851; SEQ ID NO:1), human tumor-associated antigen, L6 (GI 186804; SEQ ID NO:9), and mouse L6 antigen (GI 476343; SEQ ID NO:10). The alignment was produced using the MEGALIGN program of LASERGENE software (DNASTAR, Madison Wis.).

Figure 3B:
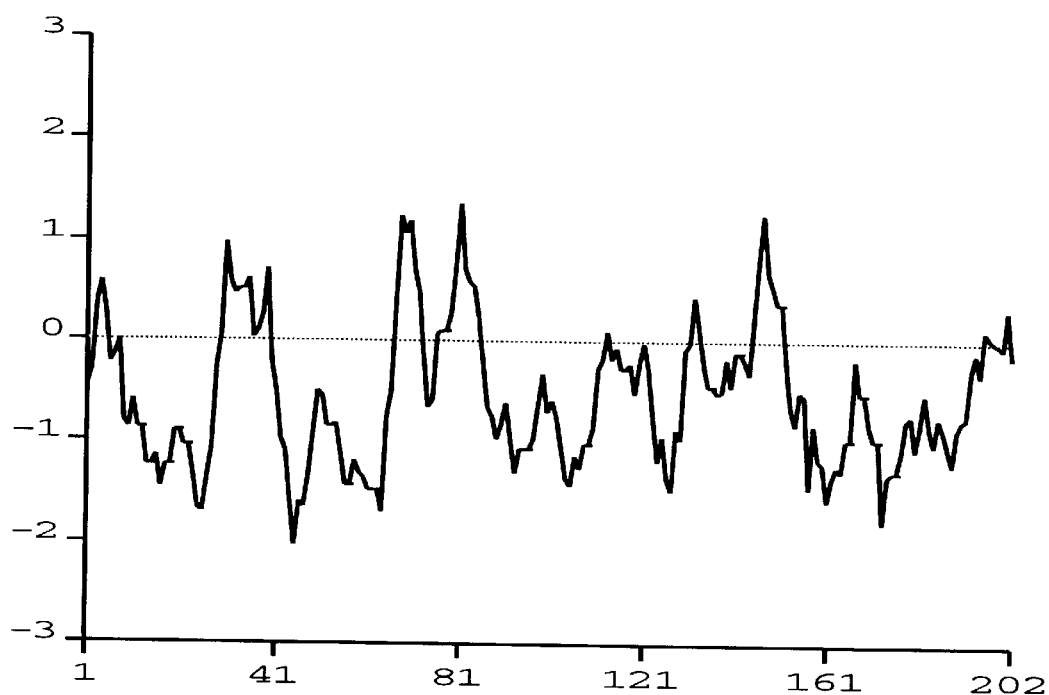

FIGS. 3A and 3B show the hydrophobicity plots (MACDNASIS PRO software) for TUAN (SEQ ID NO: 1) and the human L6 antigen (SEQ ID NO:9), respectively. The positive X axis reflects amino acid position, and the negative Y axis, hydrophobicity.

Tables 1 and 2 show the northern analysis for TUAN produced using the LIFESEQ Gold database (Incyte Genomics, Palo Alto Calif.). Table 1 shows the distribution of TUAN over various tissue categories. In Table 1, the first column presents the tissue categories; the second column, the number of clones in the tissue category; the third column, the number of libraries in which at least one transcript was found relative to the total number of libraries in that category; the fourth column, the absolute abundance of the transcript (number of transcripts); and the fifth column, percent abundance of the transcript. Table 2 shows expression of TUAN in intestinal tissues. The first column lists the library name, the second column, the number of cDNAs sequenced for that library; the third column, the description of the tissue; the fourth column, the absolute abundance of the transcript; and the fifth column, the percent abundance of the transcript.

DESCRIPTION OF THE INVENTION

It is understood that this invention is not limited to the particular machines, materials and methods described. It is also to be understood that the terminology used herein is for the purpose of describing particular embodiments and is not intended to limit the scope of the present invention which will be limited only by the appended claims. As used herein, the singular forms "a", "an", and "the" include plural reference unless the context clearly dictates otherwise. For example, a reference to "a host cell" includes a plurality of such host cells known to those skilled in the art.

Unless defined otherwise, all technical and scientific terms used herein have the same meanings as commonly understood by one of ordinary skill in the art to which this invention belongs. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"TUAN" refers to a purified protein obtained from any mammalian species, including bovine, canine, murine, ovine, porcine, rodent, simian, and preferably the human species, and from any source, whether natural, synthetic, semi-synthetic, or recombinant.

"Array" refers to an ordered arrangement of at least two cDNAs on a substrate. At least one of the cDNAs represents a control or standard, and the other, a cDNA of diagnostic or therapeutic interest. The arrangement of from about two to about 40,000 cDNAs on the substrate assures that the size and signal intensity of each labeled hybridization complex formed between each cDNA and at least one sample nucleic acid is individually distinguishable.

The "complement" of a cDNA of the Sequence Listing refers to a nucleic acid molecule which is completely complementary over its full length and which will hybridize to the cDNA or an mRNA under conditions of maximal stringency.

"cDNA" refers to an isolated polynucleotide, nucleic acid molecule, or any fragment or complement thereof. It may have originated recombinantly or synthetically, may be double-stranded or single-stranded, represents coding and noncoding 3' or 5' sequence, and generally lacks introns.

The phrase "cDNA encoding a protein" refers to a nucleotide sequence that closely aligns with sequences which encode conserved regions, motifs or domains that were identified by employing analyses well known in the art. These analyses include BLAST (Basic Local Alignment Search Tool) which provides identity within the conserved region (Altschul (1993) J Mol Evol 36: 290–300; Altschul et al. (1990) J Mol Biol 215:403–410).

A "composition" refers to the polynucleotide and a labeling moiety, a purified protein and a pharmaceutical carrier, an antibody and a labeling moiety, and the like. "Derivative" refers to a cDNA or a protein that has been subjected to a chemical modification. Derivatization of a cDNA can involve substitution of a nontraditional base such as queosine or of an analog such as hypoxanthine. These substitutions are well known in the art. Derivatization of a protein involves the replacement of a hydrogen by an acetyl, acyl, alkyl, amino, formyl, or morpholino group. Derivative molecules retain the biological activities of the naturally occurring molecules but may confer advantages such as longer lifespan or enhanced activity.

"Differential expression" refers to an increased, upregulated or present, or decreased, downregulated or absent, gene expression as detected by presence, absence or at least two-fold changes in the amount of transcribed messenger RNA or translated protein in a sample.

"Disorder" refers to conditions, diseases or syndromes in which the cDNAs and TUAN are differentially expressed. Such a disorder includes inflammatory and cell proliferative disorders, in particular, Crohn's disease and colon cancer.

"Fragment" refers to a chain of consecutive nucleotides from about 50 to about 4000 base pairs in length. Fragments may be used in PCR or hybridization technologies to identify related nucleic acid molecules and in binding assays to screen for a ligand. Such ligands are useful as therapeutics to regulate replication, transcription or translation.

A "hybridization complex" is formed between a cDNA and a nucleic acid of a sample when the purines of one molecule hydrogen bond with the pyrimidines of the complementary molecule, e.g., 5'-A-G-T-C-3' base pairs with 3'-T-C-A-G-5'. Hybridization conditions, degree of complementarity and the use of nucleotide analogs affect the efficiency and stringency of hybridization reactions.

"Labeling moiety" refers to any visible or radioactive label than can be attached to or incorporated into a cDNA or protein. Visible labels include but are not limited to anthocyanins, green fluorescent protein (GFP), β glucuronidase, luciferase, Cy3 and Cy5, and the like. Radioactive markers include radioactive forms of hydrogen, iodine, phosphorous, sulfur, and the like.

"Ligand" refers to any agent, molecule, or compound which will bind specifically to a polynucleotide or to an epitope of a protein. Such ligands stabilize or modulate the activity of polynucleotides or proteins and may be composed of inorganic and/or organic substances including minerals, cofactors, nucleic acids, proteins, carbohydrates, fats, and lipids.

"Oligonucleotide" refers a single-stranded molecule from about 18 to about 60 nucleotides in length which may be used in hybridization or amplification technologies or in regulation of replication, transcription or translation. Equivalent terms are amplimer, primer, and oligomer.

"Portion" refers to any part of a protein used for any purpose; but especially, to an epitope for the screening of ligands or for the production of antibodies.

"Post-translational modification" of a protein can involve lipidation, glycosylation, phosphorylation, acetylation, racemization, proteolytic cleavage, and the like. These processes may occur synthetically or biochemically. Biochemical modifications will vary by cellular location, cell type, pH, enzymatic milieu, and the like.

"Probe" refers to a cDNA that hybridizes to at least one nucleic acid in a sample. Where targets are single-stranded, probes are complementary single strands. Probes can be labeled with reporter molecules for use in hybridization reactions including Southern, northern, in situ, dot blot, array, and like technologies or in screening assays.

"Protein" refers to a polypeptide or any portion thereof. A "portion" of a protein refers to that length of amino acid sequence which would retain at least one biological activity, a domain identified by PFAM or PRINTS analysis or an antigenic epitope of the protein identified using Kyte-Doolittle algorithms of the PROTEAN program (DNASTAR, Madison Wis.). An "oligopeptide" is an amino acid sequence from about five residues to about 15 residues that is used as part of a fusion protein to produce an antibody.

"Purified" refers to any molecule or compound that is separated from its natural environment and is from about 60% free to about 90% free from other components with which it is naturally associated.

"Sample" is used in its broadest sense as containing nucleic acids, proteins, antibodies, and the like. A sample may comprise a bodily fluid; the soluble fraction of a cell preparation, or an aliquot of media in which cells were grown; a chromosome, an organelle, or membrane isolated or extracted from a cell; genomic DNA, RNA, or cDNA in solution or bound to a substrate; a cell; a tissue; a tissue print; a fingerprint, buccal cells, skin, or hair; and the like.

"Specific binding" refers to a special and precise interaction between two molecules which is dependent upon their structure, particularly their molecular side groups. For example, the intercalation of a regulatory protein into the major groove of a DNA molecule or the binding between an epitope of a protein and an agonist, antagonist, or antibody.

"Similarity" as applied to sequences, refers to the quantification (usually percentage) of nucleotide or residue matches between at least two sequences aligned using a standardized algorithm such as Smith-Waterman alignment (Smith and Waterman (1981) J Mol Biol 147:195–197) or BLAST2 (Altschul et al. (1997) Nucleic Acids Res 25:3389–3402). BLAST2 may be used in a standardized and reproducible way to insert gaps in one of the sequences in order to optimize alignment and to achieve a more meaningful comparison between them. Particularly in proteins, similarity is greater than identity in that conservative substitutions, for example, valine for leucine or isoleucine, are counted in calculating the reported percentage. Substitutions which are considered to be conservative are well known in the art.

"Substrate" refers to any rigid or semi-rigid support to which cDNAs or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

"Variant" refers to molecules that are recognized variations of a cDNA or a protein encoded by the cDNA. Splice variants may be determined by BLAST score, wherein the score is at least 100, and most preferably at least 400. Allelic variants have a high percent identity to the cDNAs and may differ by about three bases per hundred bases. "Single nucleotide polymorphism" (SNP) refers to a change in a single base as a result of a substitution, insertion or deletion. The change may be conservative (purine for purine) or non-conservative (purine to pyrimidine) and may or may not result in a change in an encoded amino acid or its secondary, tertiary, or quaternary structure.

THE INVENTION

The invention is based on the discovery of a cDNA which encodes TUAN and on the use of the cDNA, or fragments thereof, and protein, or portions thereof, directly or as compositions in the characterization, diagnosis, and treatment of inflammatory and cell proliferative disorders, in particular, Crohn's disease and colon cancer.

Nucleic acids encoding the TUAN of the present invention were first identified in Incyte Clone 1634851 from the colon tissue cDNA library (COLNNOT19) using a computer search for nucleotide and/or amino acid sequence alignments. SEQ ID NO:2 was derived from the following overlapping and/or extended nucleic acid sequences (SEQ ID NO:3–4): Incyte Clones 1634851 F6 (COLNNOT19) and 1634851T6 (COLNNOT19), and GenBank EST g989099 (SEQ ID NO:8). Table 1 shows the expression of the transcript across tissue categories. Table 2 shows expression of the transcript in tissues of the digestive system, colon and small intestine. Table 1 indicates that TUAN is differentially expressed in tissues of the digestive system, e.g., the total number of transcripts, 21 (Abundance, column 4), exceeds the total number of libraries in which it is found, 10 (column 3), indicating that the transcript is expressed more than once in at least one of these libraries. Indeed, Table 2 shows that TUAN is differentially expressed (Abundance more than one) in at least 5 of the 10 digestive system libraries in which TUAN was found, all 5 of which are associated with either Crohn's disease or cancer. The transcript is therefore useful in diagnostic assays for inflammatory and cell proliferative disorders, in particular, Crohn's disease and colon cancer. A fragment of the cDNA from about nucleotide 1 to about nucleotide 25 is also useful in diagnostic assays.

In one embodiment, the invention encompasses a polypeptide comprising the amino acid sequence of SEQ ID NO:1 as shown in FIGS. 1A and 1B. TUAN is 197 amino acids in length. It has four potential transmembrane domains encompassing residues L14-V30, F53-A70, V91-L112, and L162-C189, analogous to other TM4SF proteins. TUAN also has seven conserved cysteine residues at C75, C76, C80, C81, C85, C118, and C145, identical to the human and mouse L6 antigens (GI 186804 and GI 476343). In addition, TUAN has three potential N-glycosylation sites at N138-L141, N155-L158, and N179–1182, two casein kinase II phosphorylation sites at T140-D143 and S166-E 169, and one potential protein kinase C phosphorylation site at T3-K5. As shown in FIG. 2, TUAN has chemical and structural homology with a human L6 antigen (GI 186804; SEQ ID NO:9) and a mouse L6 antigen (GI 476343; SEQ ID NO:10). In particular, TUAN shares 47% identity with the human L6 antigen and 45% identity with the mouse L6 antigen. All three proteins share the four potential transmembrane domains identified above in TUAN. In addition, 2 of the 3 potential N-glycosylation sites found in TUAN, N138 and N155, are shared by at least one of the mouse and human L6 antigens. FIGS. 3A and 3B show that TUAN and the human L6 antigen have rather similar hydrophobicity plots, further illustrating the similarity in the four hydrophobic transmembrane domains. Useful antigenic epitopes extend from about R69 to about S90, from about A110 to about N121, from about T140 to about R150, and from about D188 to about H197. An antibody which specifically binds TUAN is useful in an diagnostic assay to identify inflammatory and cell proliferative disorders, in particular, Crohn's disease and colon cancer.

Mammalian variants of the cDNA encoding TUAN were identified using BLAST2 with default parameters and the ZOOSEQ databases (Incyte Genomics). These preferred variants have from about 82% to about 86% identity as shown in the table below. The first column shows the SEQ ID for the human cDNA; the second column, the SEQ IDvar for variant cDNAs; the third column, the clone number for the variant cDNAs; the fourth column, the percent identity to the human cDNA; and the fifth column, the alignment of the variant cDNA to the human cDNA.

| SEQ $ID_H$ | SEQ $ID_{Var}$ | $cDNA_{Var}$ | Identity | $Nt_H$ Alignment |
|---|---|---|---|---|
| 2 | 5 | 700275672H1 | 83% | 32–306 |
| 2 | 6 | 700308846H1 | 86% | 185–313 |
| 2 | 7 | 700308171F6 | 82% | 468–608 |

It will be appreciated by those skilled in the art that as a result of the degeneracy of the genetic code, a multitude of cDNAs encoding TUAN, some bearing minimal similarity to the cDNAs of any known and naturally occurring gene, may be produced. Thus, the invention contemplates each and every possible variation of cDNA that could be made by selecting combinations based on possible codon choices. These combinations are made in accordance with the standard triplet genetic code as applied to the polynucleotide encoding naturally occurring TUAN, and all such variations are to be considered as being specifically disclosed.

The cDNAs of SEQ ID NOs:2–7 may be used in hybridization, amplification, and screening technologies to identify and distinguish among SEQ ID NO:2 and related molecules in a sample. The mammalian cDNAs, SEQ ID NOS:2–7, may be used to produce transgenic cell lines or organisms which are model systems for human inflammatory and cell proliferative disorders, in particular, Crohn's disease and colon cancer and upon which the toxicity and efficacy of potential therapeutic treatments may be tested. Toxicology studies, clinical trials, and subject/patient treatment profiles may be performed and monitored using the cDNAs, proteins, antibodies and molecules and compounds identified using the cDNAs and proteins of the present invention.

Characterization and Use of the Invention
cDNA Libraries

In a particular embodiment disclosed herein, mRNA is isolated from mammalian cells and tissues using methods which are well known to those skilled in the art and used to prepare the cDNA libraries. The Incyte cDNAs were isolated from mammalian cDNA libraries a prepared as described in the EXAMPLES. The consensus sequences are chemically and/or electronically assembled from fragments including Incyte cDNAs and extension and/or shotgun sequences using computer programs such as PHRAP (P Green, University of Washington, Seattle Wash.), and AUTOASSEMBLER application (Applied Biosystems, Foster City Calif.). After verification of the 5' and 3' sequence, at least one representative cDNA which encodes TUAN is designated a reagent.

Sequencing

Methods for sequencing nucleic acids are well known in the art and may be used to practice any of the embodiments of the invention. These methods employ enzymes such as the Klenow fragment of DNA polymerase I, SEQUENASE, Taq DNA polymerase and thermostable T7 DNA polymerase (Amersham Pharmacia Biotech (APB), Piscataway N.J.), or combinations of polymerases and proofreading exonucleases such as those found in the ELONGASE amplification system (Life Technologies, Gaithersburg Md.). Preferably, sequence preparation is automated with machines such as the MICROLAB 2200 system (Hamilton, Reno Nev.) and the DNA ENGINE thermal cycler (MJ Research, Watertown Mass.). Machines commonly used for sequencing include the ABI PRISM 3700, 377 or 373 DNA sequencing systems (Applied Biosystems), the MEGABACE 1000 DNA sequencing system (APB), and the like. The sequences may be analyzed using a variety of algorithms well known in the art and described in Ausubel et al. (1997; *Short Protocols in Molecular Biology*, John Wiley & Sons, New York N.Y., unit 7.7) and in Meyers (1995; *Molecular Biology and Biotechnoloy*, Wiley VCH, New York N.Y., pp. 856–853).

Shotgun sequencing may also be used to complete the sequence of a particular cloned insert of interest. Shotgun strategy involves randomly breaking the original insert into segments of various sizes and cloning these fragments into vectors. The fragments are sequenced and reassembled using overlapping ends until the entire sequence of the original insert is known. Shotgun sequencing methods are well known in the art and use thermostable DNA polymerases, heat-labile DNA polymerases, and primers chosen from representative regions flanking the cDNAs of interest. Incomplete assembled sequences are inspected for identity using various algorithms or programs such as CONSED (Gordon (1998) Genome Res 8:195–202) which are well known in the art. Contaminating sequences, including vector or chimeric sequences, or deleted sequences can be removed or restored, respectively, organizing the incomplete assembled sequences into finished sequences.

Extension of a Nucleic Acid Sequence

The sequences of the invention may be extended using various PCR-based methods known in the art. For example, the XL-PCR kit (Applied Biosystems), nested primers, and commercially available cDNA or genomic DNA libraries may be used to extend the nucleic acid sequence. For all PCR-based methods, primers may be designed using commercially available software, such as OLIGO primer analysis software (Molecular Biology Insights, Cascade CO) to be about 22 to 30 nucleotides in length, to have a GC content of about 50% or more, and to anneal to a target molecule at temperatures from about 55 C to about 68 C. When extending a sequence to recover regulatory elements, it is preferable to use genomic, rather than cDNA libraries.

Hybridization

The cDNA and fragments thereof can be used in hybridization technologies for various purposes. A probe may be designed or derived from unique regions such as the 5' regulatory region or from a nonconserved region (i.e., 5' or 3' of the nucleotides encoding the conserved catalytic. domain of the protein) and used in protocols to identify naturally occurring molecules encoding the TUAN, allelic variants, or related molecules. The probe may be DNA or RNA, may be single-stranded, and should have at least 50% sequence identity to any of the nucleic acid sequences, SEQ ID NOs:2–7. Hybridization probes may be produced using oligolabeling, nick translation, end-labeling, or PCR amplification in the presence of a reporter molecule. A vector containing the cDNA or a fragment thereof may be used to produce an mRNA probe in vitro by addition of an RNA polymerase and labeled nucleotides. These procedures may be conducted using commercially available kits such as those provided by APB.

The stringency of hybridization is determined by G+C content of the probe, salt concentration, and temperature. In particular, stringency can be increased by reducing the concentration of salt or raising the hybridization temperature. Hybridization can be performed at low stringency with buffers, such as 5×SSC with 1% sodium dodecyl sulfate (SDS) at 60 C, which permits the formation of a hybridization complex between nucleic acid sequences that contain some mismatches. Subsequent washes are performed at higher stringency with buffers such as 0.2×SSC with 0.1% SDS at either 45 C (medium stringency) or 68 C (high stringency). At high stringency, hybridization complexes will remain stable only where the nucleic acids are completely complementary. In some membrane-based hybridizations, preferably 35% or most preferably 50%, formamide can be added to the hybridization solution to reduce the temperature at which hybridization is performed, and background signals can be reduced by the use of detergents such as Sarkosyl or TRITON X-100 (Sigma-Aldrich, St. Louis Mo.) and a blocking agent such as denatured salmon sperm DNA. Selection of components and conditions for hybridization are well known to those skilled in the art and are reviewed in Ausubel (supra) and Sambrook et al. (1989) *Molecular Cloning, A Laboratory Manual*, Cold Spring Harbor Press, Plainview N.Y.

Arrays may be prepared and analyzed using methods well known in the art. Oligonucleotides or cDNAs may be used as hybridization probes or targets to monitor the expression level of large numbers of genes simultaneously or to identify genetic variants, mutations, and single nucleotide polymorphisms. Arrays may be used to determine gene function; to understand the genetic basis of a condition, disease, or disorder; to diagnose a condition, disease, or disorder; and to develop and monitor the activities of therapeutic agents. (See, e.g., Brennan et al. (1995) U.S. Pat. No. 5,474,796; Schena et al. (1996) Proc Natl Acad Sci 93:10614–10619; Heller et al. (1997) Proc Natl Acad Sci 94:2150–2155; and Heller et al. (1997) U.S. Pat. No. 5,605,662.)

Hybridization probes are also useful in mapping the naturally occurring genomic sequence. The probes may be hybridized to a particular chromosome, a specific region of a chromosome, or an artificial chromosome construction. Such constructions include human artificial chromosomes (HAC), yeast artificial chromosomes (YAC), bacterial artificial chromosomes (BAC), bacterial P1 constructions, or the cDNAs of libraries made from single chromosomes.

Expression

Any one of a multitude of cDNAs encoding TUAN may be cloned into a vector and used to express the protein, or portions thereof, in host cells. The nucleic acid sequence can be engineered by such methods as DNA shuffling (U.S. Pat. No. 5,830,721) and site-directed mutagenesis to create new restriction sites, alter glycosylation patterns, change codon preference to increase expression in a particular host, produce splice variants, extend half-life, and the like. The expression vector may contain transcriptional and translational control elements (promoters, enhancers, specific initiation signals, and polyadenylated 3' sequence) from various sources which have been selected for their efficiency in a particular host. The vector, cDNA, and regulatory elements are combined using in vitro recombinant DNA techniques, synthetic techniques, and/or in vivo genetic recombination techniques well known in the art and described in Sambrook (supra, ch. 4, 8, 16 and 17).

A variety of host systems may be transformed with an expression vector. These include, but are not limited to, bacteria transformed with recombinant bacteriophage, plasmid, or cosmid DNA expression vectors; yeast transformed with yeast expression vectors; insect cell systems transformed with baculovirus expression vectors; plant cell systems transformed with expression vectors containing viral and/or bacterial elements, or animal cell systems (Ausubel supra, unit 16). For example, an adenovirus transcription/translation complex may be utilized in mammalian cells. After sequences are ligated into the E1 or E3 region of the viral genome, the infective virus is used to transform and express the protein in host cells. The Rous sarcoma virus enhancer or SV40 or EBV-based vectors may also be used for high-level protein expression.

Routine cloning, subcloning, and propagation of nucleic acid sequences can be achieved using the multifunctional PBLUESCRIPT vector (Stratagene, La Jolla Calif.) or PSPORT1 plasmid (Life Technologies). Introduction of a nucleic acid sequence into the multiple cloning site of these vectors disrupts the lacZ gene and allows colorimetric screening for transformed bacteria. In addition, these vectors may be useful for in vitro transcription, dideoxy sequencing, single strand rescue with helper phage, and creation of nested deletions in the cloned sequence.

For long term production of recombinant proteins, the vector can be stably transformed into cell lines along with a selectable or visible marker gene on the same or on a separate vector. After transformation, cells are allowed to grow for about 1 to 2 days in enriched media and then are transferred to selective media. Selectable markers, antimetabolite, antibiotic, or herbicide resistance genes, confer resistance to the relevant selective agent and allow growth and recovery of cells which successfully express the introduced sequences. Resistant clones identified either by survival on selective media or by the expression of visible markers may be propagated using culture techniques. Visible markers are also used to estimate the amount of protein expressed by the introduced genes. Verification that the host cell contains the desired cDNA is based on DNA-DNA or DNA-RNA hybridizations or PCR amplification techniques.

The host cell may be chosen for its ability to modify a recombinant protein in a desired fashion. Such modifications include acetylation, carboxylation, glycosylation, phosphorylation, lipidation, acylation and the like. Post-translational processing which cleaves a "prepro" form may also be used to specify protein targeting, folding, and/or activity. Different host cells available from the ATCC (Manassas Va.) which have specific cellular machinery and characteristic mechanisms for post-translational activities may be chosen to ensure the correct modification and processing of the recombinant protein.

Recovery of Proteins from Cell Culture

Heterologous moieties engineered into a vector for ease of purification include glutathione S-transferase (GST), 6×His, FLAG, MYC, and the like. GST and 6-His are purified using commercially available affinity matrices such as immobilized glutathione and metal-chelate resins, respectively. FLAG and MYC are purified using commercially available monoclonal and polyclonal antibodies. For ease of separation following purification, a sequence encoding a proteolytic cleavage site may be part of the vector located between the protein and the heterologous moiety. Methods for recombinant protein expression and purification are discussed in Ausubel (supra, unit 16) and are commercially available.

Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full length peptide is synthesized by sequential deprotection, coupling of derivitized amino acids, and washing with dichloromethane and/or N,N-dimethylformamide. The peptide is cleaved between the peptide carboxy terminus and the linker group to yield a peptide acid or amide. (Novabiochem 1997/98 Catalog and Peptide Synthesis Handbook, San Diego Calif. pp. S1–S20). Automated synthesis may also be carried out on machines such as the ABI 431A peptide synthesizer (Applied Biosystems). A protein or portion thereof may be purified by preparative high performance liquid chromatography and its composition confirmed by amino acid analysis or by sequencing (Creighton (1984) *Proteins, Structures and Molecular Properties*, W H Freeman, New York N.Y.).

Preparation and Screening of Antibodies

Various hosts including, but not limited to, goats, rabbits, rats, mice, and human cell lines may be immunized by injection with TUAN or any portion thereof. Adjuvants such as Freund's, mineral gels, and surface active substances such as lysolecithin, pluronic polyols, polyanions, peptides, oil emulsions, keyhole limpet hemacyanin (KLH), and dinitrophenol may be used to increase immunological response. The oligopeptide, peptide, or portion of protein used to induce antibodies should consist of at least about five amino acids, more preferably ten amino acids, which are identical to a portion of the natural protein. Oligopeptides may be fused with proteins such as KLH in order to produce antibodies to the chimeric molecule.

Monoclonal antibodies may be prepared using any technique which provides for the production of antibodies by continuous cell lines in culture. These include, but are not limited to, the hybridoma technique, the human B-cell hybridoma technique, and the EBV-hybridoma technique. (See, e.g., Kohler et al. (1975) Nature 256:495497; Kozbor et al. (1985) J. Immunol Methods 81:31–42; Cote et al. (1983) Proc Natl Acad Sci 80:2026–2030; and Cole et al. (1984) Mol Cell Biol 62:109–120.)

Alternatively, techniques described for antibody production may be adapted, using methods known in the art, to produce epitope-specific, single chain antibodies. Antibody fragments which contain specific binding sites for epitopes of the protein may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse et al. (1989) Science 246:1275–1281.)

The TUAN or a portion thereof may be used in screening assays of phagemid or B-lymphocyte immunoglobulin libraries to identify antibodies having the desired specificity. Numerous protocols for competitive binding or immunoassays using either polyclonal or monoclonal antibodies with established specificities are well known in the art. Such immunoassays typically involve the measurement of complex formation between the protein and its specific antibody. A two-site, monoclonal-based immunoassay utilizing monoclonal antibodies reactive to two non-interfering epitopes is preferred, but a competitive binding assay may also be employed (Pound (1998) *Immunochemical Protocols*, Humana Press, Totowa N.J.).

Labeling of Molecules for Assay

A wide variety of reporter molecules and conjugation techniques are known by those skilled in the art and may be used in various nucleic acid, amino acid, and antibody assays. Synthesis of labeled molecules may be achieved using commercially available kits (Promega, Madison Wis.) for incorporation of a labeled nucleotide such as $^{32}$P-DCTP (APB), Cy3-dCTP or Cy5-dCTP (Operon Technologies, Alameda Calif.), or amino acid such as $^{35}$S-methionine (APB). Nucleotides and amino acids may be directly labeled with a variety of substances including fluorescent, chemiluminescent, or chromogenic agents, and the like, by chemical conjugation to amines, thiols and other groups present in the molecules using reagents such as BIODIPY or FITC (Molecular Probes, Eugene Oreg.).

DIAGNOSTICS

Nucleic Acid Assays

The cDNAs, fragments, oligonucleotides, complementary RNA and DNA molecules, and PNAs may be used to detect and quantify differential gene expression for diagnosis of a disorder. Similarly antibodies which specifically bind TUAN may be used to quantitate the protein. Disorders associated with differential expression include inflammatory and cell proliferative disorders, in particular, Crohn's disease and colon cancer. The diagnostic assay may use hybridization or amplification technology to compare gene expression in a biological sample from a patient to standard samples in order to detect differential gene expression. Qualitative or quantitative methods for this comparison are well known in the art.

For example, the cDNA or probe may be labeled by standard methods and added to a biological sample from a patient under conditions for the formation of hybridization complexes. After an incubation period, the sample is washed and the amount of label (or signal) associated with hybridization complexes, is quantified and compared with a standard value. If complex formation in the patient sample is significantly altered (higher or lower) in comparison to either a normal or disease standard, then differential expression indicates the presence of a disorder.

In order to provide standards for establishing differential expression, normal and disease expression profiles are established. This is accomplished by combining a sample taken from normal subjects, either animal or human, with a cDNA under conditions for hybridization to occur. Standard hybridization complexes may be quantified by comparing the values obtained using normal subjects with values from an experiment in which a known amount of a purified sequence is used. Standard values obtained in this manner may be compared with values obtained from samples from patients who were diagnosed with a particular condition, disease, or disorder. Deviation from standard values toward those associated with a particular disorder is used to diagnose that disorder.

Such assays may also be used to evaluate the efficacy of a particular therapeutic treatment regimen in animal studies or in clinical trials or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to years.

Protein Assays

Detection and quantification of a protein using either labeled amino acids or specific polyclonal or monoclonal antibodies are known in the art. Examples of such techniques include two-dimensional polyacrylamide gel electrophoresis, enzyme-linked immunosorbent assays (ELISAs), radioimmunoassays (RIAs), and fluorescence activated cell sorting (FACS). These assays and their quantitation against purified, labeled standards are well known in the art (Ausubel, supra, unit 10.1–10.6).

THERAPEUTICS

Chemical and structural similarity, in particular the four transmembrane domains, exists between regions of TUAN (SEQ ID NO:1), human L6 antigen (GI 186804; SEQ ID NO:9) and mouse L6 antigen (GI 476343; SEQ ID NO:10) as shown in FIG. 2. In addition, differential expression is associated with digestive system, and with inflammatory and cell proliferative disorders, in particular, Crohn's disease and colon cancer as shown in Tables 1 and 2. TUAN clearly plays a role in Crohn's disease and colon cancer.

In the treatment of conditions associated with increased expression of the protein, it is desirable to decrease expression or protein activity. In one embodiment, the an inhibitor, antagonist or antibody of the protein may be administered to a subject to treat a condition associated with increased expression or activity. In another embodiment, a pharmaceutical composition comprising an inhibitor, antagonist, or antibody and a pharmaceutical carrier may be administered to a subject to treat a condition associated with the increased expression or activity of the endogenous protein. In an additional embodiment, a vector expressing the complement of the cDNA or fragments thereof may be administered to a subject to treat the disorder.

In the treatment of conditions associated with decreased expression of the protein, it is desirable to increase expression or protein activity. In one embodiment, the protein, an agonist or enhancer may be administered to a subject to treat a condition associated with decreased expression or activity. In another embodiment, a pharmaceutical composition comprising the protein, an agonist or enhancer and a pharmaceutical carrier may be administered to a subject to treat a condition associated with the decreased expression or activity of the endogenous protein. In an additional embodiment, a vector expressing cDNA may be administered to a subject to treat the disorder.

Any of the cDNAs, complementary molecules, or fragments thereof, proteins or portions thereof, vectors delivering these nucleic acid molecules or expressing the proteins, and their ligands may be administered in combination with other therapeutic agents. Selection of the agents for use in combination therapy may be made by one of ordinary skill in the art according to conventional pharmaceutical principles. A combination of therapeutic agents may act synergistically to affect treatment of a particular disorder at a lower dosage of each agent.

Modification of Gene Expression Using Nucleic Acids

Gene expression may be modified by designing complementary or antisense molecules (DNA, RNA, or PNA) to the control, 5', 3', or other regulatory regions of the gene encoding TUAN. Oligonucleotides designed to inhibit transcription initiation are preferred. Similarly, inhibition can be achieved using triple helix base-pairing which inhibits the binding of polymerases, transcription factors, or regulatory molecules (Gee et al. In: Huber and Carr (1994) *Molecular and Immunologic Approaches*, Futura Publishing, Mt. Kisco N.Y., pp. 163–177). A complementary molecule may also be designed to block translation by preventing binding between ribosomes and mRNA. In one alternative, a library or plurality of cDNAs may be screened to identify those which specifically bind a regulatory, nontranslated sequence.

Ribozymes, enzymatic RNA molecules, may also be used to catalyze the specific cleavage of RNA. The mechanism of ribozyme action involves sequence-specific hybridization of the ribozyme molecule to complementary target RNA followed by endonucleolytic cleavage at sites such as GUA, GUU, and GUC. Once such sites are identified, an oligonucleotide with the same sequence may be evaluated for secondary structural features which would render the oligonucleotide inoperable. The suitability of candidate targets may also be evaluated by testing their hybridization with complementary oligonucleotides using ribonuclease protection assays.

Complementary nucleic acids and ribozymes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothioate or 2' O-methyl rather than phosphodiesterase linkages within the backbone of the molecule. Modification is inherent in the production of PNAs and can be extended to other nucleic acid molecules. Either the inclusion of nontraditional bases such as inosine, queosine, and wybutosine, or the modification of adenine, cytidine, guanine, thymine, and uridine with acetyl-, methyl-, thio- groups renders the molecule less available to endogenous endonucleases.

Screening and Purification Assays

The cDNA encoding TUAN may be used to screen a library or a plurality of molecules or compounds for specific binding affinity. The libraries may be aptamers, DNA molecules, RNA molecules, PNAs, peptides, proteins such as transcription factors, enhancers, or repressors, and other ligands which regulate the activity, replication, transcription, or translation of the endogenous gene. The assay involves combining a polynucleotide with a library or plurality of molecules or compounds under conditions allowing specific binding, and detecting specific binding to identify at least one molecule which specifically binds the single-stranded or double-stranded molecule.

In one embodiment, the cDNA of the invention may be incubated with a plurality of purified molecules or compounds and binding activity determined by methods well known in the art, e.g., a gel-retardation assay (U.S. Pat. No. 6,010,849) or a reticulocyte lysate transcriptional assay. In another embodiment, the cDNA may be incubated with nuclear extracts from biopsied and/or cultured cells and tissues. Specific binding between the cDNA and a molecule or compound in the nuclear extract is initially determined by gel shift assay and may be later confirmed by recovering and raising antibodies against that molecule or compound. When these antibodies are added into the assay, they cause a supershift in the gel-retardation assay.

In another embodiment, the cDNA may be used to purify a molecule or compound using affinity chromatography methods well known in the art. In one embodiment, the cDNA is chemically reacted with cyanogen bromide groups on a polymeric resin or gel. Then a sample is passed over and reacts with or binds to the cDNA. The molecule or compound which is bound to the cDNA may be released from the cDNA by increasing the salt concentration of the flow-through medium and collected.

In a further embodiment, the protein or a portion thereof may be used to purify a ligand from a sample. A method for using a protein or a portion thereof to purify a ligand would involve combining the protein or a portion thereof with a sample under conditions to allow specific binding, detecting specific binding between the protein and ligand, recovering the bound protein, and using a chaotropic agent to separate the protein from the purified ligand.

In a preferred embodiment, TUAN may be used to screen a plurality of molecules or compounds in any of a variety of screening assays. The portion of the protein employed in such screening may be free in solution, affixed to an abiotic or biotic substrate (e.g. borne on a cell surface), or located intracellularly. For example, in one method, viable or fixed prokaryotic host cells that are stably transformed with recombinant nucleic acids that have expressed and positioned a peptide on their cell surface can be used in screening assays. The cells are screened against a plurality or libraries of ligands, and the specificity of binding or formation of complexes between the expressed protein and the ligand can be measured. Depending on the particular kind of molecules or compounds being screened, the assay may be used to identify DNA molecules, RNA molecules, peptide nucleic acids, peptides, proteins, mimetics, agonists, antagonists, antibodies, immunoglobulins, inhibitors, and drugs or any other ligand, which specifically binds the protein.

In one aspect, this invention comtemplates a method for high throughput screening using very small assay volumes and very small amounts of test compound as described in U.S. Pat. No. 5,876,946, incorporated herein by reference. This method is used to screen large numbers of molecules and compounds via specific binding. In another aspect, this invention also contemplates the use of competitive drug screening assays in which neutralizing antibodies capable of binding the protein specifically compete with a test compound capable of binding to the protein. Molecules or compounds identified by screening may be used in a mammalian model system to evaluate their toxicity, diagnostic, or therapeutic potential.

Pharmacology

Pharmaceutical compositions contain active ingredients in an effective amount to achieve a desired and intended purpose and a pharmaceutical carrier. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of protein or inhibitor which ameliorates the symptoms or condition. Therapeutic efficacy and toxicity of such agents may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it may be expressed as the ratio, $LD_{50}/ED_{50}$. Pharmaceutical compositions which exhibit large therapeutic indexes are preferred. The data obtained from cell culture assays and animal studies are used in formulating a range of dosage for human use.

Model Systems

Animal models may be used as bioassays where they exhibit a phenotypic response similar to that of humans and where exposure conditions are relevant to human exposures. Mammals are the most common models, and most infectious agent, cancer, drug, and toxicity studies are performed on rodents such as rats or mice because of low cost, availability, lifespan, reproductive potential, and abundant reference literature. Inbred and outbred rodent strains provide a convenient model for investigation of the physiological consequences of under- or over-expression of genes of interest and for the development of methods for diagnosis and treatment of diseases. A mammal inbred to over-express a particular gene (for example, secreted in milk) may also serve as a convenient source of the protein expressed by that gene.

Toxicology

Toxicology is the study of the effects of agents on living systems. The majority of toxicity studies are performed on rats or mice. Observation of qualitative and quantitative changes in physiology, behavior, homeostatic processes, and lethality in the rats or mice are used to generate a toxicity profile and to assess potential consequences on human health following exposure to the agent.

Genetic toxicology identifies and analyzes the effect of an agent on the rate of endogenous, spontaneous, and induced genetic mutations. Genotoxic agents usually have common chemical or physical properties that facilitate interaction with nucleic acids and are most harmful when chromosomal aberrations are transmitted to progeny. Toxicological studies may identify agents that increase the frequency of structural or functional abnormalities in the tissues of the progeny if administered to either parent before conception, to the mother during pregnancy, or to the developing organism. Mice and rats are most frequently used in these tests because their short reproductive cycle allows the production of the numbers of organisms needed to satisfy statistical requirements.

Acute toxicity tests are based on a single administration of an agent to the subject to determine the symptomology or lethality of the agent. Three experiments are conducted: 1) an initial dose-range-finding experiment, 2) an experiment to narrow the range of effective doses, and 3) a final experiment for establishing the dose-response curve.

Subchronic toxicity tests are based on the repeated administration of an agent. Rat and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Transgenic Animal Models

Transgenic rodents that over-express or under-express a gene of interest may be inbred and used to model human diseases or to test therapeutic or toxic agents. (See, e.g., U.S.

Pat. No. 5,175,383 and U.S. Pat. No. 5,767,337.) In some cases, the introduced gene may be activated at a specific time in a specific tissue type during fetal or postnatal development. Expression of the transgene is monitored by analysis of phenotype, of tissue-specific mRNA expression, or of serum and tissue protein levels in transgenic animals before, during, and after challenge with experimental drug therapies.

Embryonic Stem Cells

Embryonic (ES) stem cells isolated from rodent embryos retain the potential to form embryonic tissues. When ES cells are placed inside a carrier embryo, they resume normal development and contribute to tissues of the live-born animal. ES cells are the preferred cells used in the creation of experimental knockout and knockin rodent strains. Mouse ES cells, such as the mouse 129/SvJ cell line, are derived from the early mouse embryo and are grown under culture-.conditions well known in the art. Vectors used to produce a transgenic strain contain a disease gene candidate and a marker gen, the latter serves to identify the presence of the introduced disease gene. The vector is transformed into ES cells by methods well known in the art, and transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains.

ES cells derived from human blastocysts may be manipulated in vitro to differentiate into at least eight separate cell lineages. These lineages are used to study the differentiation of various cell types and tissues in vitro, and they include endoderm, mesoderm, and ectodermal cell types which differentiate into, for example, neural cells, hematopoietic lineages, and cardiomyocytes.

Knockout Analysis

In gene knockout analysis, a region of a mammalian gene is enzymatically modified to include a non-mammalian gene such as the neomycin phosphotransferase gene (neo; Capecchi (1989) Science 244:1288–1292). The modified gene is transformed into cultured ES cells and integrates into the endogenous genome by homologous recombination. The inserted sequence disrupts transcription and translation of the endogenous gene. Transformed cells are injected into rodent blastulae, and the blastulae are implanted into pseudopregnant dams. Transgenic progeny are crossbred to obtain homozygous inbred lines which lack a functional copy of the mammalian gene. In one example, the mammalian gene is a human gene.

Knockin Analysis

ES cells can be used to create knockin humanized animals (pigs) or transgenic animal-models (mice or rats) of human diseases. With knockin technology, a region of a human gene is injected into animal ES cells, and the human sequence integrates into the animal cell genome. Transformed cells are injected into blastulae and the blastulae are implanted as described above. Transgenic progeny or inbred lines are studied and treated with potential pharmaceutical agents to obtain information on treatment of the analogous human condition. These methods have been used to model several human diseases.

Non-Human Primate Model

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human surrogates in vaccine and drug evaluations, and their responses are relevant to human exposures under similar conditions. Cynomolgus and Rhesus monkeys (*Macaca fascicularis* and *Macaca mulatta*, respectively) and Common Marmosets (*Callithrix jacchus*) are the most common non-human primates (NHPs) used in these investigations. Since great cost is associated with developing and maintaining a colony of NHPs, early research and toxicological studies are usually carried out in rodent models. In studies using behavioral measures such as drug addiction, NHPs are the first choice test animal. In addition, NHPs and individual humans exhibit differential sensitivities to many drugs and toxins and can be classified as a range of phenotypes from "extensive metabolizers" to "poor metabolizers" of these agents.

In additional embodiments, the cDNAs which encode the protein may be used in any molecular biology techniques that have yet to be developed, provided the new techniques rely on properties of cDNAs that are currently known, including, but not limited to, such properties as the triplet genetic code and specific base pair interactions.

EXAMPLES

The examples below are provided to illustrate the subject invention and are not included for the purpose of limiting the invention. The preparation of the human colon (COLNNOT19) library will be described.

I cDNA Library Construction

The COLNNOT19 library was constructed using 1 microgram of poly A RNA isolated from the cecal tissue of an 18-year-old Caucasian female affected with Crohn's disease of the ileum. The frozen tissue was homogenized and lysed using a POLYTRON homogenizer (Brinkmann Instruments, Westbury N.J.) in guanidinium isothiocyanate solution. The lysate was centrifuged over a 5.7 M CsCl cushion using an SW28 rotor in an L8-70M ultracentrifuge (Beckman Coulter, Fullerton Calif.) for 18 hours at 25,000 rpm at ambient temperature. The RNA was extracted with acid phenol, pH 4.7, precipitated using 0.3 M sodium acetate and 2.5 volumes of ethanol, resuspended in RNAse-free water, and treated with DNAse at 37 C. The RNA was reextracted and precipitated as before. The mRNA was isolated with the OLIGOTEX kit (Qiagen, Chatsworth Calif.) and used to construct the cDNA library.

The mRNA was handled according to the recommended protocols in the SUPERSCRIPT plasmid system (Life Technologies) which contains a NotI primer-adaptor designed to prime the first strand cDNA synthesis at the poly(A) tail of mRNAs. Double stranded cDNA was blunted, ligated to EcoRI adaptors and digested with NotI (New England Biolabs, Beverly Mass.). The cDNAs were fractionated on a SEPHAROSE CL4B column (APB), and those cDNAs exceeding 400 bp were ligated into pINCY plasmid (Incyte Genomics). The plasmid pINCY was subsequently transformed into DH5α competent cells (Life Technologies).

II Construction of pINCY Plasmid

The plasmid was constructed by digesting the pSPORT1 plasmid (Life Technologies) with EcoRI restriction enzyme (New England Biolabs, Beverly Mass.) and filling the overhanging ends using Klenow enzyme (New England Biolabs) and 2'-deoxynucleotide 5'-triphosphates (dNTPs). The plasmid was self-ligated and transformed into the bacterial host, *E. coli* strain JM109.

An intermediate plasmid, pSPORT 1-ΔRI, which showed no digestion with EcoRI, was digested with Hind III (New England Biolabs); and the overhanging ends were filled in with Klenow and dNTPs. A linker sequence was phosphorylated, ligated onto the 5' blunt end, digested with EcoRI, and self-ligated. Following transformation into JM109 host cells, plasmids were isolated and tested for preferential digestibility with EcoRI, but not with Hind III. A single colony that met this criteria was designated pINCY plasmid.

After testing the plasmid for its ability to incorporate cDNAs from a library prepared using NotI and EcoRI restriction enzymes, several clones were sequenced; and a single clone containing an insert of approximately 0.8 kb was selected from which to prepare a large quantity of the plasmid. After digestion with NotI and EcoRI, the plasmid was isolated on an agarose gel and purified using a QIAQUICK column (Qiagen) for use in library construction.

III Isolation and Sequencing of cDNA Clones

Plasmid DNA was released from the cells and purified using either the MNIPREP kit (Edge Biosystems, Gaithersburg Md.) or the REAL PREP 96 plasmid kit (Qiagen). A kit consists of a 96-well block with reagents for 960 purifications. The recommended protocol was employed except for the following changes: 1) the bacteria were cultured in 1 ml of sterile TERRIFIC BROTH (BD Biosciences, Sparks Md.) with carbenicillin at 25 mg/l and glycerol at 0.4%; 2) after inoculation, the cells were cultured for 19 hours and then lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4 C.

The cDNAs were prepared for sequencing using the MICROLAB 2200 system (Hamilton) in combination with the DNA ENGINE thermal cyclers (MJ Research). The cDNAs were sequenced by the method of Sanger and Coulson (1975; J Mol Biol 94:441–448) using an ABI PRISM 377 sequencing system (Applied Biosystems) or the MEGABACE 1000 DNA sequencing system (APB). Most of the isolates were sequenced according to standard ABI protocols and kits (Applied Biosystems) with solution volumes of 0.25×–1.0×concentrations. In the alternative, cDNAs were sequenced using solutions and dyes from APB.

IV Extension of cDNA Sequences

The cDNAs were extended using the cDNA clone and oligonucleotide primers. One primer was synthesized to initiate 5' extension of the known fragment, and the other, to initiate 3' extension of the known fragment. The initial primers were designed using commercially available primer analysis software to be about 22 to 30 nucleotides in length, to have a GC content of about 50% or more, and to anneal to the target sequence at temperatures of about 68 C to about 72 C. Any stretch of nucleotides that would result in hairpin structures and primer-primer dimerizations was avoided.

Selected cDNA libraries were used as templates to extend the sequence. If more than one extension was necessary, additional or nested sets of primers were designed. Preferred libraries have been size-selected to include larger cDNAs and random primed to contain more sequences with 5' or upstream regions of genes. Genomic libraries are used to obtain regulatory elements, especially extension into the 5' promoter binding region.

High fidelity amplification was obtained by PCR using methods such as that taught in U.S. Pat. No. 5,932,451. PCR was performed in 96-well plates using the DNA ENGINE thermal cycler (MJ Research). The reaction mix contained DNA template, 200 nmol of each primer, reaction buffer containing $Mg^{2+}$, $(NH_4)_2SO_4$, and β-mercaptoethanol, Taq DNA polymerase (APB), ELONGASE enzyme (Life Technologies), and Pfu DNA polymerase (Stratagene), with the following parameters for primer pair PCI A and PCI B (Incyte Genomics): Step 1: 94 C, three min; Step 2: 94 C, 15 sec; Step 3: 60 C, one min; Step 4: 68 C, two min; Step 5: Steps 2, 3, and 4 repeated 20 times; Step 6: 68 C, five min; Step 7: storage In the alternative, the parameters for primer pair T7 and SK+ (Stratagene) were as follows: Step 1: 94 C, three min; Step 2: 94 C, 15 sec; Step 3: 57 C, one min; Step 4: 68 C, two min; Step 5: Steps 2, 3, and 4 repeated 20 times; Step 6: 68 C, five min; Step 7: storage at 4 C.

The concentration of DNA in each well was determined by dispensing 100 μl PICOGREEN quantitation reagent (0.25% reagent in 1×TE, v/v; Molecular Probes) and 0.5 μl of undiluted PCR product into each well of an opaque fluorimeter plate (Coming, Acton Mass.) and allowing the DNA to bind to the reagent. The plate was scanned in a Fluoroskan II (Labsystems Oy) to measure the fluorescence of the sample and to quantify the concentration of DNA. A 5 μl to 10 μl aliquot of the reaction mixture was analyzed by electrophoresis on a 1% agarose minigel to determine which reactions were successful in extending the sequence.

The extended clones were desalted, concentrated, transferred to 384-well plates, digested with CviJI cholera virus endonuclease (Molecular Biology Research, Madison Wis.), and sonicated or sheared prior to religation into pUC18 vector (APB). For shotgun sequences, the digested nucleotide sequences were separated on low concentration (0.6 to 0.8%) agarose gels, fragments were excised, and the agar was digested with AGARACE enzyme (Promega). Extended clones were religated using T4 DNA ligase (New England Biolabs) into pUC18 vector (APB), treated with Pfu DNA polymerase (Stratagene) to fill-in restriction site overhangs, and transfected into E. coli competent cells. Transformed cells were selected on antibiotic-containing media, and individual colonies were picked and cultured overnight at 37 C in 384-well plates in LB/2×carbenicillin liquid media.

The cells were lysed, and DNA was amplified using primers, Taq DNA polymerase (APB) and Pfu DNA polymerase (Stratagene) with the following parameters: Step 1: 94 C, three min; Step 2: 94 C, 15 sec; Step 3: 60 C, one min; Step 4: 72 C, two min; Step 5: steps 2, 3, and 4 repeated 29 times; Step 6: 72 C, five min; Step 7: storage at 4 C. DNA was quantified using PICOGREEN quantitation reagent (Molecular Probes) as described above. Samples with low DNA recoveries were reamplified using the conditions described above. Samples were diluted with 20% dimethylsulfoxide (DMSO; 1:2, v/v), and sequenced using DYENAMIC energy transfer sequencing primers and the DYENAMIC DIRECT cycle sequencing kit (APB) or the ABI PRISM BIGDYE terminator cycle sequencing kit (Applied Biosystems).

V Homology Searching of cDNA Clones and Their Deduced Proteins

The cDNAs of the Sequence Listing or their deduced amino acid sequences were used to query databases such as GenBank, SwissProt, BLOCKS, and the like. These databases that contain previously identified and annotated sequences or domains were searched using BLAST or BLAST2 to produce alignments and to determine which sequences were exact matches or homologs. The alignments were to sequences of prokaryotic (bacterial) or eukaryotic (animal, fungal, or plant) origin. Alternatively, algorithms such as the one described in Smith and Smith (1992, Protein Engineering 5:35–51) could have been used to deal with primary sequence patterns and secondary structure gap penalties. All of the sequences disclosed in this application have lengths of at least 49 nucleotides, and no more than 12% uncalled bases (where N is recorded rather than A, C, G, or T).

As detailed in Karlin and Altschul (1993; Proc Natl Acad Sci 90:5873–5877) BLAST matches between a query sequence and a database sequence were evaluated statistically and only reported when they satisfied the threshold of $10^{-25}$ for nucleotides and $10^{-14}$ for peptides. Homology was also evaluated by product score calculated as follows: the % nucleotide or amino acid identity [between the query and reference sequences] in BLAST is multiplied by the % maximum possible BLAST score [based pn the lengths of query and reference sequences] and then divided by 100. In comparison with hybridization procedures used in the laboratory, the stringency for an exact match was set from a lower limit of about 40 (with 1–2% error due to uncalled bases) to a 100% match of about 70.

The BLAST software suite (NCBI, Bethesda MD; http://www.ncbi.nlm.nih.gov/gorf/b12.html), includes various sequence analysis programs including "blastn" that is used to align nucleotide sequences and BLAST2 that is used for direct pairwise comparison of either nucleotide or amino acid sequences. BLAST programs are commonly used with gap and other parameters set to default settings, e.g.: Matrix: BLOSUM62; Reward for match: 1; Penalty for mismatch: –2; Open Gap: 5 and Extension Gap: 2 penalties; Gap×dropoff: 50; Expect: 10; Word Size: 11; and Filter: on. Identity is measured over the entire length of a sequence. Brenner et al. (1998; Proc Natl Acad Sci 95:6073–6078, incorporated herein by reference) analyzed BLAST for its ability to identify structural homologs by sequence identity and found 30% identity is a reliable threshold for sequence alignments of at least 150 residues and 40%, for alignments of at least 70 residues.

The cDNAs of this application were compared with assembled consensus sequences or templates found in the LIFESEQ GOLD database (Incyte Genomics). Component sequences from cDNA, extension, full length, and shotgun sequencing projects were subjected to PHRED analysis and assigned a quality score. All sequences with an acceptable quality score were subjected to various pre-processing and editing pathways to remove low quality 3' ends, vector and linker sequences, polyA tails, Alu repeats, mitochondrial and ribosomal sequences, and bacterial contamination sequences. Edited sequences had to be at least 50 bp in length, and low-information sequences and repetitive elements such as dinucleotide repeats, Alu repeats, and the like, were replaced by "Ns" or masked.

Edited sequences were subjected to assembly procedures in which the sequences were assigned to gene bins. Each sequence could only belong to one bin, and sequences in each bin were assembled to produce a template. Newly sequenced components were added to existing bins using BLAST and CROSSMATCH. To be added to a bin, the component sequences had to have a BLAST quality score greater than or equal to 150 and an alignment of at least 82% local identity. The sequences in each bin were assembled using PHRAP. Bins with several overlapping component sequences were assembled using DEEP PHRAP. The orientation of each template was determined based on the number and orientation of its component sequences.

Bins were compared to one another, and those having local similarity of at least 82% were combined and reassembled. Bins having templates with less than 95% local identity were split. Templates were subjected to analysis by STITCHER/EXON MAPPER algorithms that determine the probabilities of the presence of splice variants, alternatively spliced exons, splice junctions, differential expression of alternative spliced genes across tissue types or disease states, and the like. Assembly procedures were repeated periodically, and templates were annotated using BLAST against GenBank databases such as GBpri. An exact match was defined as having from 95% local identity over 200 base pairs through 100% local identity over 100 base pairs and a homolog match as having an E-value (or probability score) of $\leq 1 \times 10^{-8}$. The templates were also subjected to frameshift FASTx against GENPEPT, and homolog match was defined as having an E-value of $\leq 1 \times 10^{-8}$. Template analysis and assembly was described in U.S. Ser. No. 09/276,534, filed Mar. 25, 1999.

Following assembly, templates were subjected to BLAST, motif, and other functional analyses and categorized in protein hierarchies using methods described in U.S. Ser. No. 08/812,290 and U.S. Ser. No. 08/811,758, both filed Mar. 6, 1997; in U.S. Ser. No. 08/947,845, filed Oct. 9, 1997; and in U.S. Ser. No. 09/034,807, filed Mar. 4, 1998. Then templates were analyzed by translating each template in all three forward reading frames and searching each translation against the PFAM database of hidden Markov model-based protein families and domains using the HMMER software package (Washington University School of Medicine, St. Louis Mo.; http://pfam.wustl.edu/). The cDNA was further analyzed using MACDNASIS PRO software (Hitachi Software Engineering), and LASERGENE software (DNASTAR) and queried against public databases such as the GenBank rodent, mammalian, vertebrate, prokaryote, and eukaryote databases, SwissProt, BLOCKS, PRINTS, PFAM, and Prosite.

VI Chromosome Mapping

Radiation hybrid and genetic mapping data available from public resources such as the Stanford Human Genome Center (SHGC), Whitehead Institute for Genome Research (WIGR), and Généthon are used to determine if any of the cDNAs presented in the Sequence Listing have been mapped. Any of the fragments of the cDNA encoding TUAN that have been mapped result in the assignment of all related regulatory and coding sequences to the same location. The genetic map locations are described as ranges, or intervals, of human chromosomes. The map position of an interval, in cM (which is roughly equivalent to 1 megabase of human DNA), is measured relative to the terminus of the chromosomal p-arm.

VII Hybridization Technologies and Analyses
Immobilization of cDNAs on a Substrate The cDNAs are applied to a substrate by one of the following methods. A mixture of cDNAs is fractionated by gel electrophoresis and transferred to a nylon membrane by capillary transfer. Alternatively, the cDNAs are individually ligated to a vector and inserted into bacterial host cells to form a library. The cDNAs are then arranged on a substrate by one of the following methods. In the first method, bacterial cells containing individual clones are robotically picked and arranged on a nylon membrane. The membrane is placed on LB agar containing selective agent (carbenicillin, kanamycin, ampicillin, or chloramphenicol depending on the vector used) and incubated at 37 C for 16 hr. The membrane is removed from the agar and consecutively placed colony side up in 10% SDS, denaturing solution (1.5 M NaCl, 0.5 M NaOH ), neutralizing solution (1.5 M NaCl, 1 M Tris, pH 8.0), and twice in 2×SSC for 10 min each. The membrane is then UV irradiated in a STRATALINKER UV-crosslinker (Stratagene).

In the second method, cDNAs are amplified from bacterial vectors by thirty cycles of PCR using primers complementary to vector sequences flanking the insert. PCR amplification increases a starting concentration of 1–2 ng nucleic acid to a final quantity greater than 5 µg. Amplified nucleic acids from about 400 bp to about 5000 bp in length are purified using SEPHACRYL–400 beads (APB). Purified nucleic acids are arranged on a nylon membrane manually or using a dot/slot blotting manifold and suction device and are immobilized by denaturation, neutralization, and UV irradiation as described above. Purified nucleic acids are robotically arranged and immobilized on polymer-coated glass slides using the procedure described in U.S. Pat. No. 5,807, 522. Polymer-coated slides are prepared by cleaning glass microscope slides (Coming, Acton Mass.) by ultrasound in 0.1% SDS and acetone, etching in 4% hydrofluoric acid (VWR Scientific Products, West Chester Pa.), coating with 0.05% aminopropyl silane (Sigma Aldrich) in 95% ethanol, and curing in a 110 C oven. The slides are washed extensively with distilled water between and after treatments. The nucleic acids are arranged on the slide and then immobilized by exposing the array to UV irradiation using a STRATALINKER UV-crosslinker (Stratagene). Arrays are then washed at room temperature in 0.2% SDS and rinsed three times in distilled water. Non-specific binding sites are blocked by incubation of arrays in 0.2% casein in phosphate buffered saline (PBS; Tropix, Bedford Mass.) for 30 min at 60 C; then the arrays are washed in 0.2% SDS and rinsed in distilled water as before.

Probe Preparation for Membrane Hybridization

Hybridization probes derived from the cDNAs of the Sequence Listing are employed for screening cDNAs, mRNAs, or genomic DNA in membrane-based hybridizations. Probes are prepared by diluting the cDNAs to a concentration of 40–50 ng in 45 µl TE buffer, denaturing by heating to 100 C for five min, and briefly centrifuging. The denatured cDNA is then added to a REDIPRIME tube (APB), gently mixed until blue color is evenly distributed, and briefly centrifuged. Five µl of [$^{32}$P]dCTP is added to the tube, and the contents are incubated at 37 C for 10 min. The labeling reaction is stopped by adding 5 µl of 0.2M EDTA, and probe is purified from unincorporated nucleotides using a PROBEQUANT G-50 microcolumn (APB). The purified probe is heated to 100 C for five min, snap cooled for two min on ice, and used in membrane-based hybridizations as described below.

Probe Preparation for Polymer Coated Slide Hybridization

Hybridization probes derived from mRNA isolated from samples are employed for screening cDNAs of the Sequence Listing in array-based hybridizations. Probe is prepared using the GEMbright kit (Incyte Genomics) by diluting mRNA to a concentration of 200 ng in 9 µl TE buffer and adding 5 µl 5×buffer, 1 µl 0.1 M DTT, 3 µl Cy3 or Cy5 labeling mix, 1 µl RNase inhibitor, 1 µl reverse transcriptase, and 5 µl 1×yeast control mRNAs. Yeast control mRNAs are synthesized by in vitro transcription from noncoding yeast genomic DNA (W. Lei, unpublished). As quantitative controls, one set of control mRNAs at 0.002 ng, 0.02 ng, 0.2 ng, and 2 ng are diluted into reverse transcription reaction mixture at ratios of 1:100,000, 1:10,000, 1:1000, and 1:100 (w/w) to sample mRNA respectively. To examine mRNA differential expression patterns, a second set of control mRNAs are diluted into reverse transcription reaction mixture at ratios of 1:3, 3:1, 1:10, 10:1, 1:25, and 25:1 (w/w). The reaction mixture is mixed and incubated at 37 C for two hr. The reaction mixture is then incubated for 20 min at 85 C, and probes are purified using two successive CHROMA SPIN+TE 30 columns (Clontech, Palo Alto Calif.). Purified probe is ethanol precipitated by diluting probe to 90 µl in DEPC-treated water, adding 2 µl 1 mg/ml glycogen, 60 µl 5 M sodium acetate, and 300 µl 100% ethanol. The probe is centrifuged for 20 min at 20,800×g, and the pellet is resuspended in 12 µl resuspension buffer, heated to 65 C for five min, and mixed thoroughly. The probe is heated and mixed as before and then stored on ice. Probe is used in high density array-based hybridizations as described below.

Membrane-based Hybridization

Membranes are pre-hybridized in hybridization solution containing 1% Sarkosyl and 1×high phosphate buffer (0.5 M NaCl, 0.1 M Na$_2$HPO$_4$, 5 mM EDTA, pH 7) at 55 C for two hr. The probe, diluted in 15 ml fresh hybridization solution, is then added to the membrane. The membrane is hybridized with the probe at 55 C for 16 hr. Following hybridization, the membrane is washed for 15 min at 25 C in 1 mM Tris (pH 8.0), 1% Sarkosyl, and four times for 15 min each at 25 C in 1 mM Tris (pH 8.0). To detect hybridization complexes, XOMAT-AR film (Eastman Kodak, Rochester N.Y.) is exposed to the membrane overnight at −70 C, developed, and examined visually.

Polymer Coated Slide-based Hybridization

Probe is heated to 65 C for five min, centrifuged five min at 9400 rpm in a 5415 C microcentrifuge (Eppendorf Scientific, Westbury N.Y. ), and then 18 µl is aliquoted onto the array surface and covered with a coverslip. The arrays are transferred to a waterproof chamber having a cavity just slightly larger than a microscope slide. The chamber is kept at 100% humidity internally by the addition of 140 µl of 5×SSC in a corner of the chamber. The chamber containing the arrays is incubated for about 6.5 hr at 60 C. The arrays are washed for 10 min at 45 C in 1×SSC, 0.1% SDS, and three times for 10 min each at 45 C in 0.1×SSC, and dried.

Hybridization reactions are performed in absolute or differential hybridization formats. In the absolute hybridization format, probe from one sample is hybridized to array elements, and signals are detected after hybridization complexes form. Signal strength correlates with probe mRNA levels in the sample. In the differential hybridization format, differential expression of a set of genes in two biological samples is analyzed. Probes from the two samples are prepared and labeled with different labeling moieties. A mixture of the two labeled probes is hybridized to the array elements, and signals are examined under conditions in which the emissions from the two different labels are individually detectable. Elements on the array that are hybridized to equal numbers of probes derived from both biological samples give a distinct combined fluorescence (Shalon WO95/35505).

Hybridization complexes are detected with a microscope equipped with an Innova 70 mixed gas 10 W laser (Coherent, Santa Clara Calif.) capable of generating spectral lines at 488 nm for excitation of Cy3 and at 632 nm for excitation of Cy5. The excitation laser light is focused on the array using a 20×microscope objective (Nikon, Melville N.Y.). The slide containing the array is placed on a computer-controlled X-Y stage on the microscope and raster-scanned past the objective with a resolution of 20 micrometers. In the differential hybridization format, the two fluorophores are sequentially excited by the laser. Emitted light is split, based on wavelength, into two photomultiplier tube detectors (PMT R1477, Hamamatsu Photonics Systems, Bridgewater N.J.) corresponding to the two fluorophores. Filters positioned between the array and the photomultiplier tubes are used to separate the signals. The emission maxima of the fluorophores used are 565 nm for Cy3 and 650 nm for Cy5. The sensitivity of the scans is calibrated using the signal intensity generated by the yeast control mRNAs added to the probe mix. A specific location on the array contains a complementary DNA sequence, allowing the intensity of the signal at that location to be correlated with a weight ratio of hybridizing species of 1:100,000.

The output of the photomultiplier tube is digitized using a 12-bit RTI-835H analog-to-digital (A/D) conversion board (Analog Devices, Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using the emission spectrum for each fluorophore. A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS program (Incyte Genomics).

VIII Electronic Analysis

BLAST was used to search for identical or related molecules in the GenBank or LIFESEQ databases (Incyte Genomics). The product score for human and rat sequences was calculated as follows: the BLAST score is multiplied by the % nucleotide identity and the product is divided by (5 times the length of the shorter of the two sequences), such that a 100% alignment over the length of the shorter sequence gives a product score of 100. The product score takes into account both the degree of similarity between two sequences and the length of the sequence match. For example, with a product score of 40, the match will be exact within a 1% to 2% error, and with a product score of at least 70, the match will be exact. Similar or related molecules are usually identified by selecting those which show product scores between 8 and 40.

Electronic northern analysis was performed at a product score of 70 and is shown in Table 1. All sequences and cDNA libraries in the LIFESEQ database were categorized by system, organ/tissue and cell type. The categories included cardiovascular system, connective tissue, digestive system, embryonic structures, endocrine system, exocrine glands, female and male genitalia, germ cells, hemic/immune system, liver, musculoskeletal system, nervous system, pancreas, respiratory system, sense organs, skin, stomatognathic system, unclassified/mixed, and the urinary tract. For each category, the number of libraries in which the sequence was expressed were counted and shown over the total number of libraries in that category. In a non-normalized library, significant expression may reflect presence.or absence or differential expression of the cDNA.

IX Complementary Molecules

Molecules complementary to the cDNA, from about 5 (PNA) to about 5000 bp (complement of a cDNA insert), are used to detect or inhibit gene expression. Detection is described in Example VII. To inhibit transcription by preventing promoter binding, the complementary molecule is designed to bind to the most unique 5' sequence and includes nucleotides of the 5' UTR upstream of the initiation codon of the open reading frame. Complementary molecules include genomic sequences (such as enhancers or introns) and are used in "triple helix" base pairing to compromise the ability of the double helix to open sufficiently for the binding of polymerases, transcription factors, or regulatory molecules. To inhibit translation, a complementary molecule is designed to prevent ribosomal binding to the mRNA encoding the protein.

Complementary molecules are placed in expression vectors and used to transform a cell line to test efficacy; into an organ, tumor, synovial cavity, or the vascular system for transient or short term therapy; or into a stem cell, zygote, or other reproducing lineage for long term or stable gene therapy. Transient expression lasts for a month or more with a non-replicating vector and for three months or more if elements for inducing vector replication are used in the transformation/expression system.

Stable transformation of dividing cells with a vector encoding the complementary molecule produces a transgenic cell line, tissue, or organism (U.S. Pat. No. 4,736,866). Those cells that assimilate and replicate sufficient quantities of the vector to allow stable integration also produce enough complementary molecules to compromise or entirely eliminate activity of the cDNA encoding the protein.

X Expression of TUAN

Expression and purification of the protein are achieved using either a mammalian cell expression system or an insect cell expression system. The pUB6/V5-His vector system (Invitrogen, Carlsbad Calif.) is used to express TUAN in CHO cells. The vector contains the selectable bsd gene, multiple cloning sites, the promoter/enhancer sequence from the human ubiquitin C gene, a C-terminal V5 epitope for antibody detection with anti-V5 antibodies, and a C-terminal polyhistidine (6×His) sequence for rapid purification on PROBOND resin (Invitrogen). Transformed cells are selected on media containing blasticidin.

*Spodoptera frugiperda* (Sf9) insect cells are infected with recombinant *Autographica californica* nuclear polyhedrosis virus (baculovirus). The polyhedrin gene is replaced with the cDNA by homologous recombination and the polyhedrin promoter drives cDNA transcription. The protein is synthesized as a fusion protein with 6×his which enables purification as described above. Purified protein is used in the following activity and to make antibodies

XI Production of Antibodies

TUAN is purified using polyacrylamide gel electrophoresis and used to immunize mice or rabbits. Antibodies are produced using the protocols below. Alternatively, the amino acid sequence of TUAN is analyzed using LASERGENE software (DNASTAR) to determine regions of high antigenicity. An antigenic epitope, usually found near the C-terminus or in a hydrophilic region is selected, synthesized, and used to raise antibodies. Typically, epitopes of about 15 residues in length are produced using an ABI 431A peptide synthesizer (Applied Biosystems) using Fmoc-chemistry and coupled to KLH (Sigma-Aldrich) by reaction with N-maleimidobenzoyl-N-hydroxysuccinimide ester to increase antigenicity.

Rabbits are immunized with the epitope-KLH complex in complete Freund's adjuvant. Immunizations are repeated at intervals thereafter in incomplete Freund's adjuvant. After a minimum of seven weeks for mouse or twelve weeks for rabbit, antisera are drawn and tested for antipeptide activity. Testing involves binding the peptide to plastic, blocking with 1% bovine serum albumin, reacting with rabbit antisera, washing, and reacting with radio-iodinated goat anti-rabbit IgG. Methods well known in the art are used to determine antibody titer and the amount of complex formation.

XII Purification of Naturally Occurring Protein Using Specific Antibodies

Naturally occurring or recombinant protein is purified by immunoaffinity chromatography using antibodies which specifically bind the protein. An immunoaffinity column is constructed by covalently coupling the antibody to CNBr-activated SEPHAROSE resin (APB). Media containing the protein is passed over the immunoaffinity column, and the column is washed using high ionic strength buffers in the presence of detergent to allow preferential absorbance of the protein. After coupling, the protein is eluted from the column using a buffer of pH 2–3 or a high concentration of urea or thiocyanate ion to disrupt antibody/protein binding, and the protein is collected.

XIII Screening Molecules for Specific Binding with the cDNA or Protein

The cDNA, or fragments thereof, or the protein, or portions thereof, are labeled with $^{32}$P-dCTP, Cy3-dCTP, or Cy5-dCTP (APB), or with BIODIPY or FITC (Molecular Probes, Eugene Oreg.), respectively. Libraries of candidate molecules or compounds previously arranged on a substrate are incubated in the presence of labeled cDNA or protein. After incubation under conditions for either a nucleic acid or amino acid sequence, the substrate is washed, and any position on the substrate retaining label, which indicates specific binding or complex formation, is assayed, and the ligand is identified. Data obtained using different concentrations of the nucleic acid or protein are used to calculate affinity between the labeled nucleic acid or protein and the bound molecule.

XIV Two-Hybrid Screen

A yeast two-hybrid system, MATCHMAKER LexA Two-Hybrid system (Clontech Laboratories, Palo Alto Calif.), is used to screen for peptides that bind the protein of the invention. A cDNA encoding the protein is inserted into the multiple cloning site of a pLexA vector, ligated, and transformed into E. coli. cDNA, prepared from mRNA, is inserted into the multiple cloning site of a pB42AD vector, ligated, and transformed into E. coli to construct a cDNA library. The pLexA plasmid and pB42AD-cDNA library constructs are isolated from E. coli and used in a 2:1 ratio to co-transform competent yeast EGY48[p8op-lacZ] cells using a polyethylene glycol/lithium acetate protocol. Transformed yeast cells are plated on synthetic dropout (SD) media lacking histidine (-His), tryptophan (-Trp), and uracil (-Ura), and incubated at 30 C until the colonies have grown up and are counted. The colonies are pooled in a minimal volume of 1×TE (pH 7.5), replated on SD/-His/-Leu/-Trp/-Ura media supplemented with 2% galactose (Gal), 1% raffinose (Raf), and 80 mg/ml 5-bromo4-chloro-3-indolyl β-d-galactopyranoside (X-Gal), and subsequently examined for growth of blue colonies. Interaction between expressed protein and cDNA fusion proteins activates expression of a LEU2 reporter gene in EGY48 and produces colony growth on media lacking leucine (-Leu). Interaction also activates expression of β-galactosidase from the p8op-lacZ reporter construct that produces blue color in colonies grown on X-Gal.

Positive interactions between expressed protein and cDNA fusion proteins are verified by isolating individual positive colonies and growing them in SD/-Trp/-Ura liquid medium for 1 to 2 days at 30 C. A sample of the culture is plated on SD/-Trp/-Ura media and incubated at 30 C until colonies appear. The sample is replica-plated on SD/-Trp/-Ura and SD/-His/-Trp/-Ura plates. Colonies that grow on SD containing histidine but not on media lacking histidine have lost the pLexA plasmid. Histidine-requiring colonies are grown on SD/Gal/Raf/X-Gal/-Trp/-Ura, and white colonies are isolated and propagated. The pB42AD-cDNA plasmid, which contains a cDNA encoding a protein that physically interacts with the protein, is isolated from the yeast cells and characterized.

XV TUAN Assay

TUAN activity is determined in a ligand-binding assay using candidate ligand molecules in the presence of $^{125}$I-labeled TUAN. TUAN is labeled with $^{125}$I Bolton-Hunter reagent (Bolton and Hunter (1973) Biochem J 133:529–539). Candidate ligand molecules, previously arrayed in the wells of a multi-well plate, are incubated with the labeled TUAN, washed, and any wells with labeled TUAN complex are assayed. Data obtained using different concentrations of TUAN are used to calculate values for the number, affinity, and association of TUAN with the candidate molecules.

All patents and publications mentioned in the specification are incorporated by reference herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of molecular biology or related fields are intended to be within the scope of the following claims.

What is claimed is:

1. A purified antibody that specifically binds to the protein having the amino acid sequence of SEQ ID NO:1.

2. A method for using an antibody to diagnose conditions or diseases associated with expression of a protein, the method comprising:
   a) combining the antibody of claim 1 with a sample, thereby forming antibody:protein complexes; and
   b) comparing complex formation with a standard, wherein the comparison indicates expression of the protein in the sample.

3. The method of claim 2 wherein the sample is from colon.

4. The method of claim 2 wherein expression is diagnostic of Crohn's disease.

5. The method of claim 2 wherein expression is diagnostic of colon cancer.

6. A composition comprising an antibody of claim 1 and a labeling moiety.

7. A composition comprising the antibody of claim 1 and a therapeutic agent.

8. A method of using an antibody to immunopurify a protein, the method comprising:
   a) attaching the antibody of claim 1 to a substrate;
   b) exposing the antibody to a sample containing protein under conditions to allow antibody-protein complexes to form;
   c) dissociating the protein from the complex; and
   d) collecting the purified protein.

9. The antibody of claim 1 wherein the antibody is selected from a monoclonal, a polyclonal, and a single chain antibody.

10. A method for using a composition to assess efficacy of a molecule or compound, the method comprising:
    a) treating a sample containing the protein having the amino acid sequence of SEQ ID NO:1 with a molecule or compound;
    b) contacting the sample with the composition of claim 6 under conditions for complex formation;
    c) determining the amount of complex formation; and
    d) comparing the amount of complex formation in the treated sample with standards, wherein the comparison indicates efficacy of the molecule or compound.

11. A method for using a composition to assess toxicity of a molecule or compound, the method comprising:
    a) treating a sample containing protein having the amino acid sequence of SEQ ID NO:1 with a molecule or compound;
    b) contacting the sample with the composition of claim 6 under conditions for complex formation;
    c) determining the amount of complex formation; and
    d) comparing the amount of complex formation in the treated sample with standards, wherein the comparison indicates toxicity of the molecule or compound.

* * * * *